US012134650B2

(12) United States Patent
Dekel et al.

(10) Patent No.: US 12,134,650 B2
(45) Date of Patent: Nov. 5, 2024

(54) COMPOSITIONS TARGETING GABRA2 AND METHODS FOR DIAGNOSIS AND TREATMENT OF CANCER

(71) Applicants: Tel HaShomer Medical Research Infrastructure and Services Ltd., Ramat-Gan (IL); Tageza Biopharmaceuticals Ltd., Tel Aviv (IL)

(72) Inventors: Benjamin Dekel, Tel-Aviv (IL); Orit Harari-Steinberg, RaAnana (IL); Sanja Goldberg, Ramat HaSharon (IL)

(73) Assignees: Tel HaShomer Medical Research Infrastructure and Services Ltd., Ramat-Gan (IL); Tageza Biopharmaceuticals Ltd., Tel Aviv (IL)

( * ) Notice: Subject to any disclaimer, the term of this patent is extended or adjusted under 35 U.S.C. 154(b) by 814 days.

(21) Appl. No.: 17/263,251

(22) PCT Filed: Jul. 25, 2019

(86) PCT No.: PCT/IL2019/050849
§ 371 (c)(1),
(2) Date: Jan. 26, 2021

(87) PCT Pub. No.: WO2020/021556
PCT Pub. Date: Jan. 30, 2020

(65) Prior Publication Data
US 2021/0163591 A1 Jun. 3, 2021

(51) Int. Cl.
| | |
|---|---|
| *A61K 35/17* | (2015.01) |
| *A61K 47/68* | (2017.01) |
| *C07K 16/28* | (2006.01) |
| *C12Q 1/6886* | (2018.01) |
| *G01N 33/574* | (2006.01) |

(52) U.S. Cl.
CPC ............ *C07K 16/286* (2013.01); *A61K 35/17* (2013.01); *A61K 47/6803* (2017.08); *A61K 47/6849* (2017.08); *C12Q 1/6886* (2013.01); *G01N 33/57492* (2013.01); *C12Q 2600/158* (2013.01); *G01N 2333/70571* (2013.01)

(58) Field of Classification Search
CPC .................................................. C07K 16/286
USPC ...................................................... 424/172.1
See application file for complete search history.

(56) References Cited

U.S. PATENT DOCUMENTS

| | | | |
|---|---|---|---|
| 2006/0204503 A1 | 9/2006 | Fitchett et al. | |
| 2017/0198359 A1 | 7/2017 | Huang et al. | |
| 2017/0320960 A1* | 11/2017 | Williams | ................ A61P 15/00 |
| 2017/0335407 A1 | 11/2017 | An et al. | |

FOREIGN PATENT DOCUMENTS

| | | |
|---|---|---|
| JP | 2015-188425 | 11/2015 |
| WO | WO 2005/005601 | 1/2005 |
| WO | WO 2019/094955 | 5/2019 |
| WO | WO 2020/021556 | 1/2020 |
| WO | WO 2021/024263 | 2/2021 |

OTHER PUBLICATIONS

Di Rosa et al (Acta Histochemica, 2015, 117: 477-485).*
Gross et al (PLoS ONE. 2015, 10(11): e0142618).*
Gura (Science, 1997, 278:1041-1042).*
Lengeling et al (Genome Research, 1999, 9(8): 732-738).*
International Search Report and the Written Opinion Dated Oct. 7, 2019 From the International Searching Authority Re. Application No. PCT/IL2019/050849. (11 Pages).
International Search Report and the Written Opinion Dated Nov. 19, 2020 From the International Searching Authority Re. Application No. PCT/IL2020/050864. (14 Pages).
Abcam "Anti-GABAA Receptor Alpha 2/GABRA2 Antibody [N399/19] Ab193311", Abcam, Product Datasheet, 3 P., Mar. 23, 2015.
Ailles et al. "Cancer Stem Cells in Solid Tumors", Current Opinion in Biotechnology, 18(5): 460-466, Oct. 2007.
Charfi et al. "Identification of GPM6A and GPM6B as Potential New Human Lymphoid Leukemia-Associated Oncogenes", Cellular Oncology, 37(3): 179-191, Published Online Jun. 12, 2014.
Chen et al. "Screening Feature Genes of Lung Carcinoma With DNA Microarray Analysis", International Journal of Clinical and Experimental Medicine, 8(8): 12161-12171, Published Online Aug. 15, 2015.
Dekel et al. "Multiple Imprinted and Stemness Genes Provide A Link Between Normal and Tumor Progenitor Cells of the Developing Human Kidney", Cancer Research, 66(12): 6040-6049, Jun. 15, 2006.
Golan et al. "In Vivo Expansion of Cancer Stemness Affords Novel Cancer Stem Cell Targets: Malignant Rhabdoid Tumor as an Example", Stem Cell Reports, 11(3):795-810, Sep. 11, 2018.
Moore et al. "Quiescent, Slow-Cycling Stem Cell Populations in Cancer: A Review of the Evidence and Discussion of Significance", Journal of Oncology, 2011(Art.ID 396076): 1-11, Published Online Sep. 29, 2010.
Pode-Shakked et al. "Developmental Tumourigenesis: NCAM as A Putative Marker for the Malignant Renal Stem/Progenitor Cell Population", Journal of Cellular and Molecular Medicine, XP002581529, 13(8B): 1792-1808, Published Online Dec. 16, 2008.
Shukrun et al. "Wilms' Tumor Blastemal Stem Cells Dedifferentiate to Propagate the Tumor Bulk", Stem Cell Reports, 3(1): 24-33, Published Online Jun. 26, 2014.
Yu et al. "Identification and Characterization of A Murine Model of BCR ABL1+ Acute B Lymphoblastic Leukemia With Central Nervous System Metastasis", Oncology Reports, 42(2): 521-532, Published Online Jun. 3, 2019.

\* cited by examiner

*Primary Examiner* — Sean E Aeder

(57) ABSTRACT

Methods of treating cancer are provided. Accordingly, there is provided a method of treating cancer in a subject in need thereof, the method comprising administering to the subject an effective amount of an agent capable of (i) specifically binding GABRA2, the agent comprising a therapeutic moiety; and/or (ii) downregulating activity and/or expression of said GABRA2. Also provided are compositions, article of manufactures and methods of diagnosing cancer and monitoring cancer treatment.

3 Claims, 10 Drawing Sheets

Specification includes a Sequence Listing.

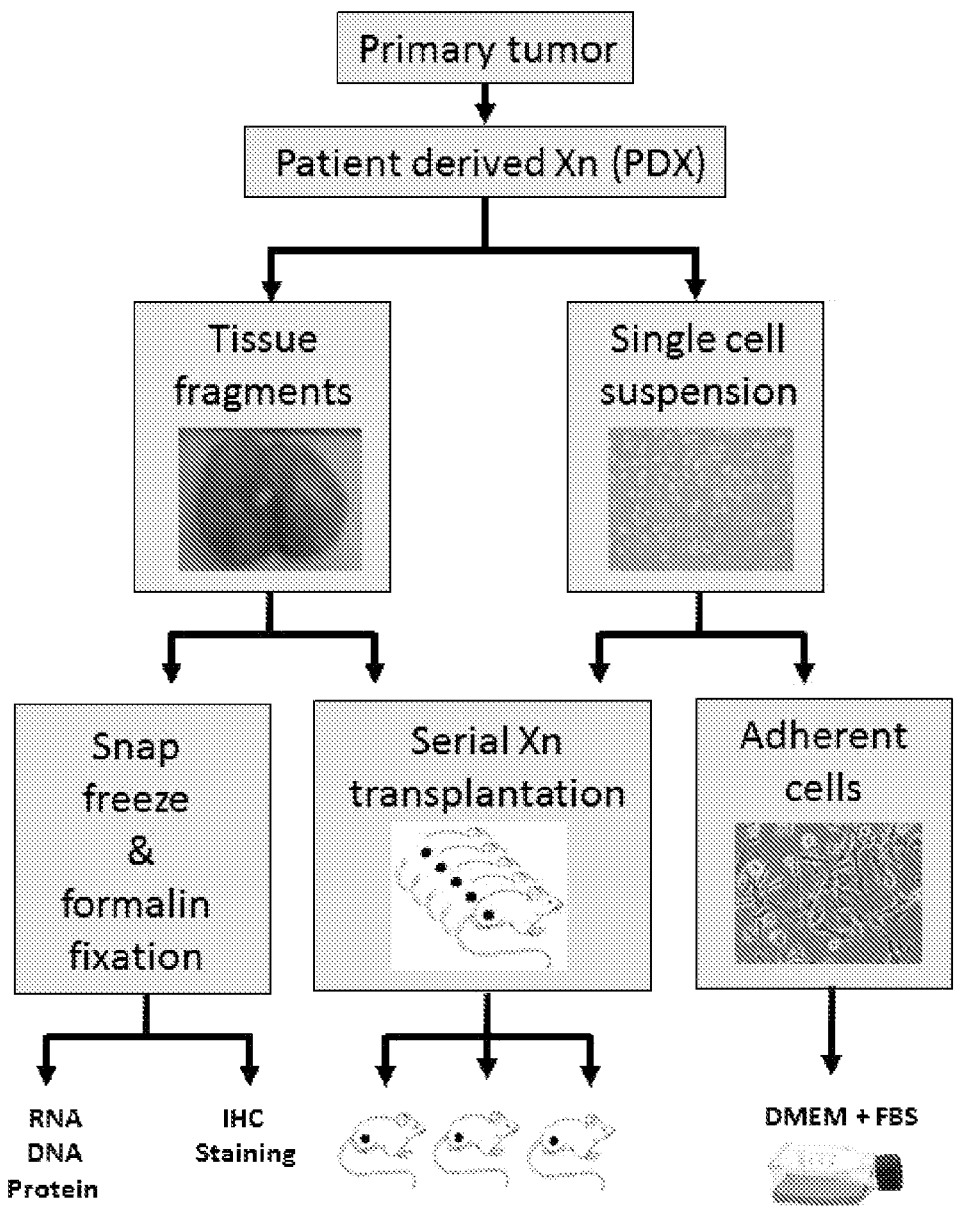

Figure 6

Signal sequence-FR1-CDR1-FR2-CDR2-FR3-CDR3-FR4

ATGAAATGCAGCTGGGTTATCTTCTTCCTGATGGCAGTGGTTACAGGGGTCAATTCAGAGGTTCAGCTGCAGCAGTCTGGGGCAGAGCTTGTGAAGCCAGGGGCCTCAGTCAAGTTGTCCTGCACAGCTTCTGGCTTCAACATTAAAGACACCTATATGTATTGGGTGAAGCAGAGGCCTGAACAGGGCCTGGAGTGGATTGGAAGGATTGATCCTGCGAATGGTAATACTAAATATGACCCGAAGTTCCAGGGCAAGGCCACTATAACAGCAGACACATCCTCCAACACAGCCTACCTGCAGCTCAGCAGCCTGACATCTGAGGACACTGCCGTCTATTACTGTGCTAGTAATTACTACGGGTCCTTTGACTACTGGGGCCAAGGCACCACTCTCACAGTCTCCTCA (SEQ ID NO: 1)

MKCSWVIFFLMAVVTGVNSEVQLQQSGAELVKPGASVKLSCTASGFNIKDTYMYWVKQRPEQGLEWIGRIDPANGNTKYDPKFQGKATITADTSSNTAYLQLSSLTSEDTAVYYCASNYYGSFDYWGQGTTLTVSS (SEQ ID NO: 6)

Figure 7

Signal sequence-FR1-CDR1-FR2-CDR2-FR3-CDR3-FR4

ATGTCCTCTGCTCAGTTCCTTGGTCTCCTGTTGCTCTGTTTTCAAGGTACCAGATGTGATATCCAGATGACACAGACTACATCCTCCCTGTCTGCCTCTCTGGGAGACAGAGTCACCATCAGTTGCAGGGCAAGTCAGGACATTAGCAATTATTTAAACTGGTATCAGCAGAAACCAGATGGAACTGTTAAACTCCTGATCTACTACACATCAAGATTACACTCAGGAGTCCCATCAAGGTTCAGTGGCAGTGGGTCTGGAACAGATTATTCTCTCACCATTAGCAACCTGGAGCAAGAAGATATTGCCACTTACTTTTGCCAACAGGGTAATACGCTTCCTCCGACGTTCGGTGGAGGCACCAAGCTGGAAATCAAA (SEQ ID NO: 11)

MSSAQFLGLLLLCFQGTRCDIQMTQTTSSLSASLGDRVTISCRASQDISNYLNWYQQKPDGTVKLLIYYTSRLHSGVPSRFSGSGSGTDYSLTISNLEQEDIATYFCQQGNTLPPTFGGGTKLEIK (SEQ ID NO: 16)

ND METHODS FOR DIAGNOSIS AND
COMPOSITIONS TARGETING GABRA2 AND METHODS FOR DIAGNOSIS AND TREATMENT OF CANCER

RELATED APPLICATIONS

This application is a National Phase of PCT Patent Application No. PCT/IL2019/050849 having International filing date of Jul. 25, 2019, which claims the benefit of priority under 35 USC § 119(e) of U.S. Provisional Patent Application No. 62/703,494 filed on Jul. 26, 2018. The contents of the above applications are all incorporated by reference as if fully set forth herein in their entirety.

SEQUENCE LISTING STATEMENT

The ASCII file, entitled 86490SequenceListing.txt, created on 2021,26 Jan., comprising 16,284 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to compositions targeting GABRA2 and methods for diagnosis and treatment of cancer.

Recent years have witnessed the exciting discoveries of cancer stem cells (CSCs), also known as tumor initiating cells (TICs), in solid tumors. Applying principles established from stem cell research, human CSCs are functionally defined by their enriched capacity to regenerate cancers using xenograft (Xn) mouse models. Similar to normal stem cells, CSCs can reproduce themselves through the process of self-renewal, which can be studied in serial transplantation assays. Additionally, cancers derived from purified CSCs recapitulate the heterogeneous phenotypes of the parental cancer from which they were derived, reflecting the differentiation capacity of CSCs. Current knowledge suggests that CSCs have crucial roles in cancer treatment failure, cancer recurrence and metastasis, due to their resistance to drug therapy, quiescent phenotype, migratory ability and evasion of the immune system (Moore 2011).

Identification of CSCs is a complex task especially in view of the fact that they are typically expressed in very low numbers in the tumor cells. Several methodologies have been performed to identify and isolate CSCs: The most commonly used assays are prospective isolation based on surface marker expression followed by functional and tumorigenicity assays (Ailles and Weissman, 2007; Pode-Shakked et al., 2009). In cases in which surgical samples are extremely rare, patient derived xenografts (PDX) have been utilized to first establish a renewable tissue source and then analyze for the presence of CSCs (Pode-Shakked et al., 2009: Dekel et al., 2006a; Shukrun et al., 2014; and International Patent Application Publication No: WO2015/198334).

GABRA2 is an alpha subunit that is part of GABA-A receptors, which are ligand-gated chloride channels and are activated by GABA, the major inhibitory neurotransmitter in the mammalian brain.

SUMMARY OF THE INVENTION

According to an aspect of some embodiments of the present invention there is provided a method of treating cancer in a subject in need thereof, the method comprising administering to the subject an effective amount of an agent capable of:
 (i) specifically binding GABRA2, the agent comprising a therapeutic moiety; and/or
 (ii) downregulating activity and/or expression of the GABRA2,
thereby treating the cancer.

According to an aspect of some embodiments of the present invention there is provided an agent capable of:
 (i) specifically binding GABRA2, the agent comprising a therapeutic moiety; and/or
 (ii) downregulating activity and/or expression of the GABRA2,
for use in treating cancer in s subject in need thereof.

According to an aspect of some embodiments of the present invention there is provided an isolated agent capable of specifically binding GABRA2, the agent comprising a heterologous therapeutic moiety.

According to an aspect of some embodiments of the present invention there is provided an antibody comprising an antigen recognition domain which specifically binds GABRA2 and comprises complementarity determining regions (CDRs) as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody.

According to some embodiments of the invention, the antibody comprising a heterologous therapeutic moiety.

According to an aspect of some embodiments of the present invention there is provided an article of manufacture comprising a cancer therapy and an agent capable of:
 (i) specifically binding GABRA2, the agent comprising a therapeutic moiety; and/or
 (ii) downregulating activity and/or expression of the GABRA2.

According to an aspect of some embodiments of the present invention there is provided an article of manufacture comprising a cancer therapy and the antibody.

According to an aspect of some embodiments of the present invention there is provided a method of treating cancer in a subject in need thereof, the method comprising administering to the subject an effective amount of the agent or the antibody, thereby treating the cancer.

According to an aspect of some embodiments of the present invention there is provided the agent or the antibody, for use in treating cancer in a subject in need thereof.

According to an aspect of some embodiments of the present invention there is provided a method of diagnosing cancer in a subject, the method comprising determining a level of GABRA2 in a biological sample of the subject, wherein the level of the GABRA2 above a predetermined threshold is indicative of cancer.

According to an aspect of some embodiments of the present invention there is provided a method of monitoring efficacy of cancer therapy in a subject, the method comprising determining a level of GABRA2 in a biological sample of the subject following the cancer therapy, wherein a decrease from a predetermined threshold in the level of the GABRA2 following the cancer therapy indicates efficaciousness of the cancer therapy.

According to an aspect of some embodiments of the present invention there is provided a method of predicting an efficacy of a cancer therapy for treatment of a subject, the method comprising:

(a) contacting a biological sample of the subject with a therapeutically effective amount of the cancer therapy; and
(b) determining a level of GABRA2 in the biological sample of the subject following the contacting with the cancer therapy;

wherein a decreased level of expression of the GABRA2 following the contacting with the cancer therapy relative to a level of expression of the GABRA2 prior to the contacting with the cancer therapy indicates that the cancer therapy is efficient for treating the subject, thereby predicting efficacy of the cancer therapy.

According to an aspect of some embodiments of the present invention there is provided a method of treating cancer in a subject in need thereof, the method comprising:
(a) diagnosing the subject according to the method; and wherein when the level of the GABRA2 above a predetermined threshold is indicated,
(b) selecting a cancer therapy based on the level of the GABRA2,
thereby treating the cancer.

According to an aspect of some embodiments of the present invention there is provided a method of treating cancer in a subject in need thereof, the method comprising:
(a) diagnosing the subject according to the method; and wherein when the level of the GABRA2 above a predetermined threshold is indicated,
(b) treating the subject with a cancer therapy,
thereby treating the cancer.

According to an aspect of some embodiments of the present invention there is provided a method of treating cancer in a subject in need thereof, the method comprising:
(a) diagnosing the subject according to the method; and wherein when the level of the GABRA2 above a predetermined threshold is indicated,
(b) administering to the subject an effective amount of an agent capable of:
  (i) specifically binding the GABRA2, the agent comprising a therapeutic moiety; and/or
  (ii) downregulating activity and/or expression of the GABRA2,
thereby treating the cancer.

According to an aspect of some embodiments of the present invention there is provided a method of treating cancer in a subject in need thereof, the method comprising:
(a) diagnosing the subject according to the method; and wherein when the level of the GABRA2 above a predetermined threshold is indicated,
(b) administering to the subject an effective amount of the antibody,
thereby treating the cancer.

According to some embodiments of the invention, the cancer therapy comprises an agent capable of:
(i) specifically binding GABRA2, the agent comprising a therapeutic moiety; and/or
(ii) downregulating activity and/or expression of the GABRA2.

According to some embodiments of the invention, the cancer therapy comprises the antibody.

According to some embodiments of the invention, the cancer therapy consists of an agent capable of:
(i) specifically binding GABRA2, the agent comprising a therapeutic moiety; and/or
(ii) downregulating activity and/or expression of the GABRA2.

According to some embodiments of the invention, the cancer therapy consists of the antibody.

According to some embodiments of the invention, the method comprising administering a cancer therapy to the subject.

According to some embodiments of the invention, the agent for use or the antibody for use comprising a cancer therapy.

According to some embodiments of the invention, the administering or the treating consists of the agent or the antibody.

According to some embodiments of the invention, the therapeutic moiety is a heterologous therapeutic moiety.

According to some embodiments of the invention, the therapeutic moiety is selected from the group consisting of a toxin, a drug, a chemical, a protein and a radioisotope.

According to some embodiments of the invention, the therapeutic moiety is capable of eliciting an immune response to a cell presenting the GABRA2 polypeptide on its cell surface.

According to some embodiments of the invention, the agent is an antibody.

According to some embodiments of the invention, the antibody comprises an antigen recognition domain which specifically binds GABRA2 and comprises complementarity determining regions (CDRs) as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody.

According to some embodiments of the invention, the agent is a T cell.

According to some embodiments of the invention, the T cell is transduced with a T cell receptor (TCR) or a chimeric antigen receptor (CAR).

According to some embodiments of the invention, the agent is a small molecule, a peptide, or an RNA silencing agent.

According to some embodiments of the invention, the cancer is a solid cancer.

According to some embodiments of the invention, the cancer is a pediatric cancer.

According to some embodiments of the invention, the cancer is an aggressive cancer.

According to some embodiments of the invention, the cancer is a metastatic cancer.

According to some embodiments of the invention, the cancer is a relapsed cancer.

According to some embodiments of the invention, the cancer has undergone epithelial to mesenchymal transition (EMT).

According to some embodiments of the invention, the cancer has a stem cell origin.

According to some embodiments of the invention, the cancer is an embryonal cancer.

According to some embodiments of the invention, the cancer is selected from the group consisting of malignant rhabdoid tumor (MRT), atypical teratoid/rhabdoid tumor (ATRT), pulmonary blastoma, Ewing sarcoma, osteosarcoma, Wilms' tumor, Medulloblastoma, renal cell carcinoma, ovarian cancer and breast cancer According to some embodiments of the invention, the cancer is selected from the group consisting of malignant rhabdoid tumor (MRT), atypical teratoid/rhabdoid tumor (ATRT), Medulloblastoma, Ewing sarcoma, renal cell carcinoma, ovarian cancer, Wilms' tumor and breast cancer.

According to some embodiments of the invention, the cancer is malignant rhabdoid tumor (MRT).

According to specific embodiments, the cancer is glioblastoma or glioma.

According to some embodiments of the invention, the cancer is not a central nervous system (CNS) cancer.

According to some embodiments of the invention, the GABRA2 is a GABRA2 polypeptide.

According to specific embodiments of the invention, the agent binds an extracellular domain of the GABRA2.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic representation of the xenograft (Xn) model. Primary tumor grafts were formed by a subcutaneous transplantation of 2-5 mm tumor pieces into immunodeficient NOD-SCID mice. Sequential propagation of PDX in NOD-SCID mice was performed by tissue samples transplantation or single cell suspensions grafting. Serial propagation allowed us to establish early (<P5), intermediate (P5-P10) and late-passage (P10-P15) PDX. Tissue fragments were also used for IHC staining, RNA, DNA and protein isolation. Adherent cells were also used for in vitro studies of the tumor's cells.

FIG. 2A is a graph demonstrating mRNA expression levels in early, intermediate and late MRT PDX. FIG. 2B is a graph demonstrating mRNA expression levels in ALDH1A1+ and ALDH1A1− sub-populations sorted from serially propagated (Xn9) MRT.

FIGS. 3A-D shows representative images from each tumor sample. FIG. 3E is a graph demonstrating the immunohistochemistry score for each tumor sample.

FIG. 5A is a graph demonstrating affinity measurement of GABRA2 to antibody U6882DH130_13. FIG. 5B is a graph demonstrating single-dose kinetics of GABRA2 to antibody U6882DH130_13.

FIG. 6 is a schematic representation of the nucleic acid and amino acid sequences of the heavy chain of antibody U6882DH130_13 (SEQ ID NO: 1 and 6, respectively). Shown are the signal sequence, the FRs (underlined) and the CDRs (bold).

FIG. 7 is a schematic representation of the nucleic acid and amino acid sequences of the light chain of antibody U6882DH130_13 (SEQ ID NO: 11 and 16, respectively). Shown are the signal sequence, the FRs (red, underlined) and the CDRs (blue, bold).

DESCRIPTION OF SPECIFIC EMBODIMENTS OF THE INVENTION

The present invention, in some embodiments thereof, relates to compositions targeting GABRA2 and methods for diagnosis and treatment of cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Cancer stem cells (CSC) represent malignant cell subsets in hierarchically organized tumors, which are selectively capable of tumor initiation and self-renewal. Current knowledge suggests that CSCs have crucial roles in cancer treatment failure, cancer recurrence and metastasis, due to their resistance to drug therapy, quiescent phenotype, migratory ability and evasion of the immune system.

Identification of CSCs is a complex task especially in view of the fact that they are typically expressed in very low numbers in the tumor cells. In pediatric solid tumors, the limited access to multiple fresh tumor specimens compounds this problem, further impeding robust CSC analysis and efficient development of novel therapeutic strategies.

As is illustrated hereinunder and in the examples section, which follows, the present inventors have identified GABRA2 as a novel CSC marker using sequential propagation of tumor derived xenografts (PDX) from malignant rhabdoid tumor (MRT) (Example 1, FIGS. 1, 2A-B and 3A-E).

Figure 4:
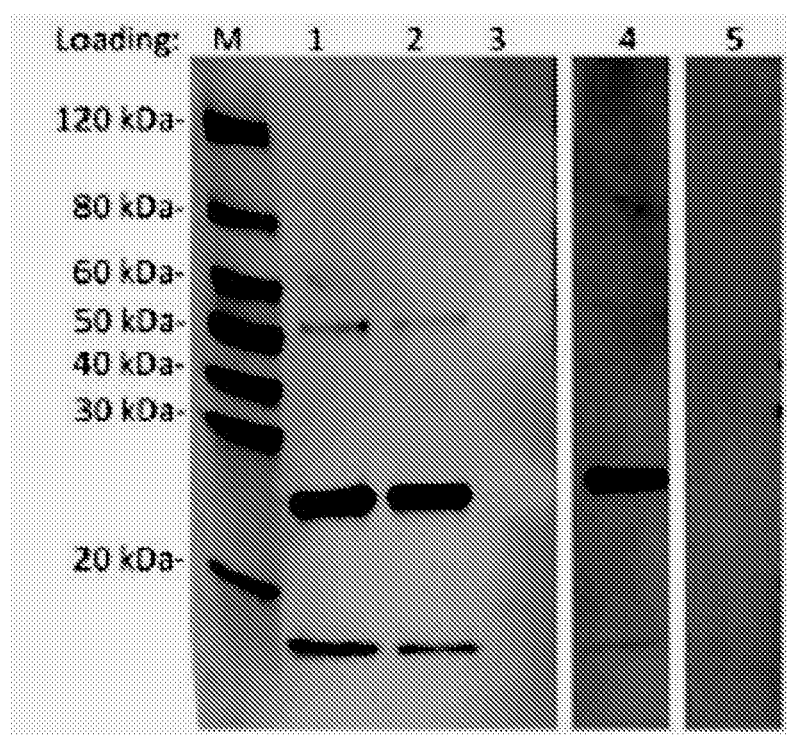
FIG. 4 demonstrates western blot analysis of an antibody, referred to herein as U6882DH130_13, purified from a hybridoma referred to herein as 10C5B9. Lanes 1, 4 and 5: 100 ng GABRA2 protein, Lane 2: 50 ng GABRA2 protein, Lane 3: 100 ng His tagged protein. Primary antibody: Lanes 1-3: 1 μg/ml purified U6882DH130_13. Lane 4: mouse antiserum against GABRA2 (1: 100), lane 5: blank. Secondary antibody: 0.125 μg/ml goat anti-mouse IgG (H&L) antibody (IRDye800cw, Licor, Cat No: 926-32210).

Consequently, according to some embodiments, the identified GABRA2 can be used as a therapeutic and diagnostic target for cancer in general and pediatric cancer in particular. To this end, as is illustrated hereinunder and in the Examples section, which follows, the present inventors have also generated an anti-human GABRA2 monoclonal antibody which targets the extracellular domain of this protein (Example 2, FIGS. 4-6).

Thus, according to a first aspect of the present invention, there is provided a method of treating cancer in a subject in need thereof, the method comprising administering to the subject an effective amount of an agent capable of:
(i) specifically binding GABRA2, the agent comprising a therapeutic moiety; and/or
(ii) downregulating activity and/or expression of said GABRA2,
thereby treating the cancer.

According to another aspect of the present invention, there is provided an agent capable of:
  (i) specifically binding GABRA2, the agent comprising a therapeutic moiety; and/or
  (ii) downregulating activity and/or expression of said GABRA2,
for use in treating cancer in s subject in need thereof.

As used herein the term "treating" refers to inhibiting, preventing or arresting the development of a pathology (disease, disorder, or condition e.g., cancer e.g., pediatric cancer, e.g. malignant rhabdoid tumor, breast cancer, glioma, glioblastoma) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

According to specific embodiments, treatment may be evaluated by a decrease in tumor volume, a decrease in the number of tumor cells, a decrease in the number of metastases, an increase in life expectancy, or amelioration of various physiological symptoms associated with the cancerous condition.

According to specific embodiments, "treating" refers to the ability of the medicament of some embodiments of the invention in prevention of the occurrence of tumor in the first place.

Cancers which may be diagnosed, monitored and/or treated by some embodiments of the invention can be any solid or non-solid cancer and/or cancer metastasis.

According to specific embodiments, the cancer is a solid cancer.

Examples of cancer include but are not limited to, carcinoma, lymphoma, blastoma, sarcoma, and leukemia. More particular examples of such cancers include, but not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer, triple negative breast cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

According to a specific embodiments, the cancer is a pediatric cancer.

Examples of pediatric solid tumors include but are not limited to Wilms' tumor, Nephroblastoma, rhabdomyosarcoma, Ewing's family of tumors/primitive neuroectodermal tumor, Osteosarcoma, peripheral neuroectodermal tumors, Childhood Germ Cell Tumor, Extragonadal Germ Cell Tumor, Kidney Cancer, malignant rhabdoid tumor (MRT), atypical teratoid/rhabdoid tumor (ATRT), pulmonary blastoma, Liver Cancer, Neuroblastoma, Ovarian Cancer, Retinoblastoma, Sarcoma, more specifically, Osteosarcoma, Rhabdomyosarcoma, Desmoplastic small round-cell tumor, Hepatoblastoma, Germ cell tumors, neuroblastoma, diffuse intrinsic pontine glioma (DIPG), and Medulloblastoma.

According to a specific embodiment, the cancer is a solid tumor having a stem cell origin.

According to a specific embodiment, the cancer is a solid tumor having an embryonic stem cell origin.

Examples of such solid tumors include, but are not limited to, sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, triple negative breast cancer, malignant rhabdoid tumor (MRT), pulmonary blastoma and retinoblastoma.

According to specific embodiments, the cancer is an aggressive cancer (i.e. forms, grows, or spreads/metastizes rapidly). Non-limiting examples of aggressive cancers include pancreatic cancer, triple negative breast cancer, metastatic renal cell carcinoma, lung cancer, ovarian cancer, aggressive prostate cancer.

According to specific embodiments, the aggressive cancer has a 10-year survival rate of 1-20%, 1-10% or 1-5%.

According to specific embodiments, the aggressive cancer has a 5-year survival rate of 1-40%, 1-30%, 1-20%, 1-15%, 1-10%, 1-7% or 1-5%.

According to specific embodiments, the aggressive cancer has a 1-year survival rate of 1-50%, 1-40%, 1-30%, 1-20%, 1-10% or 1-5%.

According to specific embodiments, the cancer is a metastatic cancer.

According to specific embodiments, the cancer is a relapsed cancer.

According to specific embodiments, the cancer has undergone epithelial to mesenchymal transition (EMT, i.e. undergone a phenotypic switch towards a mesenchymal undifferentiated state). Non-limiting examples of such cancers include triple negative breast cancer, pancreatic cancer, metastatic renal cell carcinoma, lung cancer, aggressive prostate cancer.

According to specific embodiments, the cancer is an embryonal cancer. Non-limiting examples of such cancers include Wilms' tumor, Nephroblastoma, rhabdomyosarcoma, Ewing's family of tumors/primitive neuroectodermal tumor, Osteosarcoma, peripheral neuroectodermal tumors, Childhood Germ Cell Tumor, Extragonadal Germ Cell Tumor, Kidney Cancer, malignant rhabdoid tumor (MRT), atypical teratoid/rhabdoid tumor (ATRT), pulmonary blastoma, Liver Cancer, Neuroblastoma, Ovarian Cancer, Retinoblastoma, Sarcoma, more specifically, Osteosarcoma, Rhabdomyosarcoma, Desmoplastic small round-cell tumor, Hepatoblastoma, Germ cell tumors, neuroblastoma and Medulloblastoma.

According to specific embodiments, the cancer is an adult cancer. Non-limiting examples of such cancers are disclosed hereinabove.

According to a specific embodiment, the cancer is selected from the group consisting of malignant rhabdoid tumor (MRT), atypical teratoid/rhabdoid tumor (ATRT), pulmonary blastoma, Ewing sarcoma, osteosarcoma, Wilms' tumor, Medulloblastoma, renal cell carcinoma, ovarian cancer and breast cancer (e.g. triple negative breast cancer), each possibility represents a separate embodiment of the present invention.

According to a specific embodiment, the cancer is selected from the group consisting of malignant rhabdoid tumor (MRT), atypical teratoid/rhabdoid tumor (ATRT), Medulloblastoma, Ewing sarcoma, breast cancer (e.g. triple negative breast cancer), renal cell carcinoma, ovarian cancer and Wilms' tumor, each possibility represents a separate embodiment of the present invention.

According to specific embodiments, the cancer is malignant rhabdoid tumor (MRT).

According to specific embodiments, the cancer is not colon cancer.

According to specific embodiments, the cancer is not lung cancer.

According to specific embodiments, the cancer is not ATRT.

According to specific embodiments, the cancer is not MRT.

According to specific embodiments, the cancer is not ATRT and not MRT. According to specific embodiments, the cancer is glioblastoma or glioma.

According to specific embodiments the cancer is not a central nervous (CNS) cancer. Such CNS cancers include for example, brain stem glioma, craniopharyngioma, Medulloblastoma and meningioma.

As used herein the term "subject" refers to a mammal (e.g., human being) at any age or of any gender.

According to specific embodiments, the subject is a human subject.

According to specific embodiments, the subject is diagnosed with a disease (i.e., cancer) or is at risk of to develop a disease (i.e. cancer).

According to other specific embodiments, the subject is a healthy subject undergoing a routine well-being checkup.

According to specific embodiments, the subject is at risk of having cancer (e.g., a genetically predisposed subject, a subject with medical and/or family history of cancer, a subject who has been exposed to carcinogens, occupational hazard, environmental hazard) and/or exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness].

According to specific embodiments, the subject presents an increased level of GABRA2 in a biological sample compared to a control sample obtained from a healthy subject, as further described hereinbelow.

According to specific embodiments, the subject presents an increased level above a predetermined threshold of GABRA2 in a biological sample, as further described hereinbelow.

As used herein, the term "GABRA2 (Gamma-aminobutyric acid receptor subunit alpha-2)" refers to the expression product e.g. RNA or polypeptide of the GABRA2 gene (Gene ID: 2555). According to specific embodiments, the GABRA2 refers to the human GABRA2, such as provided in the following Accession Numbers: NM_000807, NM_001114175, NM_001286827, NM_001330690, NP_000798, NP_001107647, NP_001273756, NP_001317619. According to specific embodiments, GABRA2 amino acid sequence comprises SEQ ID NO: 22.

According to specific embodiments, GABRA2 activity is at least regulating chloride (Cl—) transport.

Methods of determining transport activity are well known in the art and include, but not limited to, radiolabeled compounds, liquid scintillation counter, electrophysiological recording, chloride titration.

According to specific embodiments, GABRA2 is a cancer stem cell marker that distinguishes a cancer stem cell from other cells, such as other cancer cells present in the primary tumor and/or non-cancerous cells.

As used herein, the term "cancer stem cell (CSC)" refers to a cell capable of undergoing mitotic division and differentiating into one or more types of cell found in a tumor and includes a totipotent, pluripotent, multipotent, oligopotent and unipotent cell. CSCs have the capacity to regenerate cancers using xenograft (Xn) mouse models; and cancers derived from purified CSCs recapitulate the heterogeneous phenotypes of the parental cancer from which they were derived, reflecting the differentiation capacity of CSCs.

According to specific embodiments, GABRA2 is a GABRA2 polypeptide.

According to specific embodiments, the GABRA2 is human.

The agent of some embodiments of the present invention targets GABRA2 such that the agent is capable of specifically binding GABRA2.

The agent of some embodiments of the present invention targets GABRA2 such that the agent is capable of:
 (i) specifically binding GABRA2, the agent comprising a therapeutic moiety; and/or
 (ii) downregulating activity and/or expression of GABRA2.

According to specific embodiments, the agent is a single agent.

According to specific embodiments, the agent is at least one agent.

According to specific embodiments, the agent directly binds GABRA2, i.e. specifically binds GABRA2.

According to other specific embodiments, the agent indirectly binds GABRA2 by acting through an intermediary molecule, for example the agent binds to or modulates a molecule that in turn binds to or modulates GABRA2.

According to specific embodiments, the agent binds the extracellular domain of GABRA2.

Thus, according to specific embodiments, the agent binds amino acids residues 29 to 251 of SEQ ID NO: 22.

According to specific embodiments, the agent binds SEQ ID NO: 21.

Thus, according to specific embodiments, the agent binds an upstream activator or a downstream effector of GABRA2.

Methods of determining binding of the agent to a target are well known in the art and include BiaCore, HPLC, Surface Plasmon Resonance assay (SPR) and flow cytometry.

According to specific embodiments, the agent binds the target (e.g. GABRA2) with an affinity higher than $10^{-6}$ M.

According to specific embodiments, the agent binds the target (e.g. GABRA2) with an affinity higher than about, $10-9$ M, $10^{-10}$ M and as such is stable under physiological (e.g., in vivo) conditions.

According to a specific embodiment the affinity is between $0.1 \cdot 10^{-9}$ M or $1 \cdot 10 \times 10^{-9}$ M or $0.1 \cdot 10 \times 10^{-9}$ M. According to specific embodiments affinity is of at least 100 nM, 50 nM, 10 nM, 1 nM or higher.

According to specific embodiments, the affinity is between $1 \cdot 5 \times 10^{-10}$ M, e.g. $2 \cdot 4 \times 10^{'} 10$ M, e.g. about $3.88 \times 10^{-10}$ M.

Non limiting examples of agents that can be used with some embodiments of the invention include, but are not limited to, antibodies, T cells, small molecules, peptides, RNA silencing agents, chemicals, toxins and drugs, as further described in details hereinbelow.

According to specific embodiments, the agent is an antibody.

Preferably, the antibody specifically binds at least one epitope of GABRA2.

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

According to specific embodiments, the agent binds an epitope found on the extracellular domain of GABRA2.

According to specific embodiments, the antibody comprises an antigen recognition domain which specifically binds GABRA2 and comprises complementarity determining regions (CDRs) as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody.

Thus, according to an aspect of the present invention, there is provided an antibody comprising an antigen recognition domain which specifically binds GABRA2 and comprises CDRs as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody.

According to specific embodiments, the light chain amino acid sequence of the antibody comprises an amino acid sequence as set forth in SEQ ID NO: 16 or 17.

According to specific embodiments, the heavy chain amino acid sequence of the antibody comprises an amino acid sequence as set forth in SEQ ID NO: 6 or 7.

According to specific embodiments, the light chain amino acid sequence of the antibody comprises an amino acid sequence as set forth in SEQ ID NO: 16 or 17 and the heavy chain amino acid sequence of the antibody comprises an amino acid sequence as set forth in SEQ ID NO: 6 or 7.

The term "antibody" as used in this invention includes intact molecules as well as functional fragments thereof (such as Fab, F(ab')2, Fv, scFv, dsFv, or single domain molecules such as VH and VL) that are capable of binding to an epitope of an antigen. According to specific embodiments, the antibodies of some embodiments of the present invention bind the peptide in an MHC restricted manner. These antibodies are referred to as T cell receptor like antibodies.

According to specific embodiments, the antibody is a whole or intact antibody.

According to specific embodiments, the antibody is an antibody fragment.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv Fv (scFv), a disulfide-stabilized Fv (dsFv), an Fab, an Fab', and an F(ab')2.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys@, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "variable regions" and "CDRs" may refer to variable regions and CDRs defined by any approach known in the art, including combinations of approaches.

According to specific embodiments, the identity of the amino acid residues in the antibody that make up the variable region and/or the CDRs is determined by the method of Kabat et al. (See, e.g., Kabat et al., 1992, Sequences of Proteins of Immunological Interest, 5th ed., Public Health Service, NIH, Washington D.C.).

Functional antibody fragments comprising whole or essentially whole variable regions of both light and heavy chains are defined as follows:
  (i) Fv, defined as a genetically engineered fragment consisting of the variable region of the light chain (VL) and the variable region of the heavy chain (VH) expressed as two chains;
  (ii) single chain Fv ("scFv"), a genetically engineered single chain molecule including the variable region of the light chain and the variable region of the heavy chain, linked by a suitable polypeptide linker as a genetically fused single chain molecule.
  (iii) disulfide-stabilized Fv ("dsFv"), a genetically engineered antibody including the variable region of the light chain and the variable region of the heavy chain, linked by a genetically engineered disulfide bond.
  (iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CHI domains thereof;
  (v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);
  (vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and
  (vii) Single domain antibodies or nanobodies are composed of a single VH or VL domains which exhibit sufficient affinity to the antigen.

According to specific embodiments the antibody heavy chain constant region is chosen from, e.g., IgG1, IgG2, IgG3, IgG4, IgM, IgA1, IgA2, IgD, and IgE.

According to specific embodiments, the antibody is an IgG antibody.

According to a specific embodiment the antibody isotype is IgG1 or IgG4.

According to a specific embodiment the antibody is IgG2 e.g. IgG2b e.g. IgG2b kappa.

The choice of antibody type will depend on the immune effector function that the antibody is designed to elicit.

According to specific embodiments, the antibody comprises an Fc domain.

According to specific embodiments, the antibody is a naked antibody.

As used herein, the term "naked antibody" refers to an antibody which does not comprise a heterologous effector moiety e.g. therapeutic moiety, detectable moiety.

According to specific embodiments, the antibody comprises a heterologous effector moiety e.g. e.g. therapeutic moiety, detectable moiety. The effector moiety can be proteinaceous or non-proteinaceous; the latter generally being generated using functional groups on the antibody and on the conjugate partner. The effector moiety may be any molecule, including small molecule chemical compounds and polypeptides. Non-limiting examples of effector moieties include but are not limited to cytokines, cytotoxic antibodies, toxins, radioisotopes, chemotherapeutic antibody, anti-angiogenic antibodies, tyrosine kinase inhibitors, and other therapeutically active antibodies. Additional description on heterologous therapeutic moieties is further provided hereinbelow.

The antibody may be mono-specific (capable of recognizing one epitope or protein), bi-specific (capable of binding two epitopes or proteins) or multi-specific (capable of recognizing multiple epitopes or proteins).

According to specific embodiments, the antibody is a mono-specific antibody.

According to specific embodiments, the antibody is a multi-specific e.g. bi-specific, tri-specific, tetra-specific.

According to specific embodiments, the antibody is a bi-specific antibody. Bi-specific antibodies are antibodies that are capable of specifically recognizing and binding at least two different epitopes. The different epitopes can either be within the same molecule or on different molecules such that the bi-specific antibody can specifically recognize and bind two different epitopes on a single GABRA2 polypeptide as well as two different polypeptides. Alternatively, a bi-specific antibody can bind e.g. GABRA2 and another effector molecule such as, but not limited to e.g. CD2, CD3, CD28, B7, CD64, CD32, CD16. Methods of producing bi-specific antibodies are known in the art and disclosed for examples in U.S. Pat. Nos. 4,474,893, 5,959,084, and 7,235,641, 7,183,076, U.S. Publication Number 20080219980 and International Publication Numbers WO 2010/115589, WO2013150043 and WO2012118903 all incorporated herein by their entirety; and include, for example, chemical cross-linking (Brennan, et al., Science 229, 81 (1985); Raso, et al., J. Bio. Chem. 272, 27623 (1997)), disulfide exchange, production of hybrid-hybridomas (quadromas), by transcription and translation to produce a single polypeptide chain embodying a bi-specific antibody, or by transcription and translation to produce more than one polypeptide chain that can associate covalently to produce a bi-specific antibody. The contemplated bi-specific antibody can also be made entirely by chemical synthesis.

Antibodies with more than two valencies are also contemplated.

According to other specific embodiments, the antibody is a multi-specific antibody.

According to specific embodiments, the antibody is a conjugate antibody (i.e. an antibody composed of two covalently joined antibodies).

The antibody may be monoclonal or polyclonal.

According to specific embodiments, the antibody is a monoclonal antibody.

According to specific embodiments, the antibody is a polyclonal antibody.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

It will be appreciated that for human therapy or diagnostics, humanized antibodies are preferably used.

According to specific embodiments, the antibody is a humanized antibody. Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

According to specific embodiments, the antibody is a human antibody.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Once antibodies are obtained, they may be tested for activity, for example via ELSA.

Alternatively or additionally, antibodies which may be used in accordance with specific embodiments of the present teachings may be commercially purchased from e.g. Cell Signaling Technology, R&D, Abcam and BioLegend.

The antibody may be soluble or non-soluble.

Non-soluble antibodies may be a part of a particle (synthetic or non-synthetic) or a cell.

According to other specific embodiments, the agent is a T cell.

Preferably, the T cell is a T cell with specificity to GABRA2 antigen.

As used herein the term "T cell" refers to a differentiated lymphocyte with a $CD3^+$, T cell receptor $(TCR)^+$ having either $CD4^+$ or $CD8^+$ phenotype. The T cell may be either an effector or a regulatory T cells.

According to specific embodiments, the T cell is a CD8+ cytotoxic T cell (CTL).

According to other specific embodiments, the T cell is a CD4+ helper T cell.

According to specific embodiments, the T cells is transduced with a T cell receptor (TCR) or a chimeric antigen receptor (CAR).

As used herein the phrase "transduced with a T cell receptor (TCR)" refers to cloning of variable α- and β-chains from T cells with specificity against a specific (e.g. GABRA2) antigen presented in the context of MHC. Method of transducing with a TCR are known in the art and are disclosed e.g. in Nicholson et al. Adv Hematol. 2012; 2012:404081; Wang and Rivibre Cancer Gene Ther. 2015 March; 22(2):85-94); and Lamers et al, Cancer Gene Therapy (2002) 9, 613-623.

As used herein the phrase "transduced with a chimeric antigen receptor (CAR)" refers to cloning of a nucleic acid sequence encoding a chimeric antigen receptor (CAR).

As used herein the phrase "chimeric antigen receptor (CAR)" refers to a recombinant or synthetic molecule which combines antibody-based specificity for a desired antigen with a T cell receptor-activating intracellular domain to generate a chimeric protein that exhibits cellular immune activity to the specific antigen.

Method of transducing with a CAR are known in the art and are disclosed e.g. in Davila et al. Oncoimmunology. 2012 Dec. 1; 1(9):1577-1583; Wang and Riviere Cancer Gene Ther. 2015 March; 22(2):85-94); and Maus et al. Blood. 2014 Apr. 24; 123(17):2625-35.

According to specific embodiments, the agent is a small molecule, a peptide or an RNA silencing agent.

According to specific embodiments, the agent is a small molecule, a peptide or an RNA silencing agent which specifically binds GABRA2.

The terms "peptide" and "polypeptide" as used herein encompass native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells, as further described in details hereinbelow.

According to specific embodiments, the peptide is no more than 50 amino acids in length.

According to specific embodiments, the peptide is between 9-50 amino acids, 9-40 amino acids, 9-30 amino acids, 9-20 amino acids, or between 9-13 amino acids long.

As mentioned, according to specific embodiments the agent is capable of downregulating activity and/or expression of GABRA2.

Down-regulating activity and/or expression can be can be effected at the protein level (e.g., antibodies, small molecules, inhibitory peptides, enzymes that cleave the polypeptide, aptamers and the like) but may also be effected at the genomic (e.g. homologous recombination and site specific endonucleases) and/or the transcript level using a variety of molecules which interfere with transcription and/or translation (e.g., RNA silencing agents) of a target expression product described herein.

Down-regulation of expression may be either transient or permanent.

Methods of screening and identification of a GABRA2 inhibitor are well known in the art. For example, a screening method may comprise a cell culture wherein the cells are over expressing GABRA2. The cell culture is then exposed to at least one candidate inhibitory compound and the expression of GABRA2 is measured by e.g. RT-PCR, Western blot, ELISA or Flow cytometry.

According to specific embodiments, down-regulating expression refers to the absence of mRNA and/or protein, as detected by RT-PCR or Western blot, respectively.

According to other specific embodiments down-regulating expression refers to a decrease in the level of mRNA and/or protein, as detected by RT-PCR or Western blot, respectively. The reduction may be by at least a 10%, at least 20%, at least 30%, at least 40%, at least 50%, at least 60%, at least 70%, at least 80%, at least 90%, at least 95% or at least 99% reduction.

Non-limiting examples of down-regulating agents are described in details hereinbelow.

Down-Regulating at the Polypeptide Level

According to specific embodiments, the down-regulating agent is an antibody. A detailed description on antibodies that can be used according to specific embodiments of the present invention is provided hereinabove and below.

Another down-regulating agent which can be used along with some embodiments of the invention is an aptamer. As used herein, the term "aptamer" refers to double stranded or single stranded RNA molecule that binds to specific molecular target, such as a protein. Various methods are known in the art which can be used to design protein specific aptamers. The skilled artisan can employ SELEX (Systematic Evolution of Ligands by Exponential Enrichment) for efficient selection as described in Stoltenburg R, Reinemann C, and Strehlitz B (Biomolecular engineering (2007) 24(4): 381-403).

Another down-regulating agent would be any molecule which interferes with the target protein activity (e.g., catalytic or interaction) by binding the target protein or intermediate thereof and/or cleaving the target protein. Such molecules can be a small molecule, antagonists, or inhibitory peptide.

Another down-regulating agent which can be used along with some embodiments of the invention is a molecule which prevents target activation or substrate binding.

According to a specific embodiment, the down-regulating agent is a small molecule.

According to a specific embodiment, the down-regulating agent is a peptide molecule.

It will be appreciated that a non-functional analogue of at least a catalytic or binding portion of the target can be also used as a down-regulating agent.

Down-Regulating at the Nucleic Acid Level

Down-regulation at the nucleic acid level is typically effected using a nucleic acid agent, having a nucleic acid backbone, DNA, RNA, mimetics thereof or a combination of same. The nucleic acid agent may be encoded from a DNA molecule or provided to the cell per se.

Thus, downregulation can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include non-coding RNA molecules, for example RNA duplexes comprising paired strands, as well as precursor RNAs from which such small non-coding RNAs can be generated. Exemplary RNA silencing agents include dsRNAs, siRNAs, shRNAs, miRNAs, miRNA mimics and antisense.

In one embodiment, the RNA silencing agent is capable of inducing RNA interference.

RNA interference refers to the process of sequence-specific post-transcriptional gene silencing in animals mediated by short interfering RNAs (siRNAs).

In another embodiment, the RNA silencing agent is capable of mediating translational repression.

According to an embodiment of the invention, the RNA silencing agent is specific to the target RNA (e.g., GABRA2) and does not cross inhibit or silence other targets or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene; as determined by PCR, Western blot, Immunohistochemistry and/or flow cytometry.

Nucleic acid agents can also operate at the DNA level as summarized infra.

Downregulation can also be achieved by inactivating the gene via introducing targeted mutations involving loss-of function alterations (e.g. point mutations, deletions and insertions) in the gene structure.

As used herein, the phrase "loss-of-function alterations" refers to any mutation in the DNA sequence of a gene which results in downregulation of the expression level and/or activity of the expressed product, i.e., the mRNA transcript and/or the translated protein. Non-limiting examples of such loss-of-function alterations include a missense mutation, a nonsense mutation, a frame-shift mutation, a readthrough mutation due to a frame-shift mutation or a modified stop codon mutation with an abolished enzymatic activity, a promoter mutation, a regulatory mutation, a deletion mutation, an insertion mutation, an inversion, a mutation which results in abnormal splicing or poor splicing, and a duplication mutation.

According to specific embodiments loss-of-function alteration of a gene may comprise at least one allele of the gene.

According to other specific embodiments loss-of-function alteration of a gene comprises both alleles of the gene.

Methods of introducing nucleic acid alterations to a gene of interest are well known in the art [see for example Menke D. Genesis (2013) 51:-618; Capecchi, Science (1989) 244: 1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination (e.g. "Hit and run", "double-replacement"), site specific recombinases (e.g. the Cre recombinase and the Flp recombinase), PB transposases (e.g. Sleeping Beauty, piggyBac, Tol2 or Frog Prince), genome editing by engineered nucleases (e.g. meganucleases, Zinc finger nucleases (ZFNs), transcription-activator like effector nucleases (TALENs) and CRISPR/Cas system) and genome editing using recombinant adeno-associated virus (rAAV) platform. Agents for introducing nucleic acid alterations to a gene of interest can be designed publically available sources or obtained commercially from Transposagen, Addgene and Sangamo Biosciences.

Any of the agents described herein can comprise a detectable or a therapeutic moiety; that can be used for example in both diagnosis and treating methods.

Thus, according to specific embodiments the agent is bound to a detectable moiety.

Examples of detectable moieties that can be used in the present invention include but are not limited to radioactive isotopes, phosphorescent chemicals, chemiluminescent chemicals, fluorescent chemicals, enzymes, fluorescent polypeptides, a radioactive isotope (such as $^{[125]}$iodine) and epitope tags. The detectable moiety can be a member of a binding pair, which is identifiable via its interaction with an additional member of the binding pair, and a label which is directly visualized. In one example, the member of the binding pair is an antigen which is identified by a corresponding labeled antibody. In one example, the label is a fluorescent protein or an enzyme producing a colorimetric reaction.

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293: Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, U K. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the agent [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

Exemplary identifiable moieties include, but are not limited to green fluorescent protein, alkaline phosphatase, peroxidase, histidine tag, biotin, orange fluorescent protein and strepavidin.

Further examples of detectable moieties, include those detectable by Positron Emission Tomography (PET) and Magnetic Resonance Imaging (MRI), all of which are well known to those of skill in the art.

According to specific embodiments the agent comprises a therapeutic moiety.

The therapeutic moiety can be an integral part of the agent e.g., in the case of a whole antibody, the Fc domain, which activates antibody-dependent cell-mediated cytotoxicity (ADCC) and/or complement mediated toxicity (CDC). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. For example, eosinophils can kill certain parasitic worms known as helminths through ADCC mediated by IgE. ADCC is part of the adaptive immune response due to its dependence on a prior antibody response. CDC is an effector function of IgG and IgM antibodies. When these antibodies bound to surface antigen, the classical complement pathway is triggered, resulting in formation of a membrane attack complex (MAC) and target cell lysis.

Thus, according to specific embodiments, the therapeutic moiety is capable of eliciting antibody dependent cell toxicity toward a cell presenting the GABRA2 polypeptide on its cell surface.

According to some embodiments of the invention, the therapeutic moiety is capable of eliciting complement-dependent cytotoxicity in a cell presenting the GABRA2 polypeptide on its cell surface.

Alternatively or additionally, the agent may be a bispecific antibody (see e.g., Withoff, S., Helfrich, W., de Leij, L F., Molema, G. (2001) Curr Opin Mol Ther. 3:53-62) in which the therapeutic moiety is a T cell engager for example, such as an anti-CD3 antibody or an anti-CD16a, alternatively the therapeutic moiety may be an anti-immune checkpoint molecule (anti PD-1).

Alternatively or additionally the agent may be attached to a heterologous therapeutic moiety (exemplary methods of conjugation are described hereinbelow).

Hence, according to an aspect of the present invention there is provided an isolated agent capable of specifically binding GABRA2, the agent comprising a heterologous therapeutic moiety.

According to specific embodiments, the agent is for use in treating cancer.

The therapeutic moiety can be proteinaceous or non-proteinaceous.

The Therapeutic moiety may be any molecule, including small molecule chemical compounds and polypeptides.

Non-limiting examples of therapeutic moieties which can be used with specific embodiments of the invention include a cytotoxic moiety, a toxic moiety [e.g., Pseudomonas exotoxin (GenBank Accession Nos. AAB25018 and S53109); PE38KDEL; Diphtheria toxin (GenBank Accession Nos. E00489 and E00489); Ricin A toxin (GenBank Accession Nos. 225988 and A23903)], a cytokine moiety [e.g., interleukin 2 (GenBank Accession Nos. CAA00227 and A02159), interleukin 10 (GenBank Accession Nos. P22301 and M57627), interleukin 4 (GenBank Accession Nos. NP_000580 and NM_000589], a drug, a chemical, a protein and/or a radioisotope.

According to specific embodiments, the therapeutic moiety is selected from the group consisting of a toxin, a drug, a chemical, a protein and a radioisotope.

According to specific embodiments, the agent is a T cell receptor (TCR) or a chimeric antigen receptor (CAR) and the heterologous moiety is a T cell transduced with the agent.

According to specific embodiments, the therapeutic moiety is capable of eliciting an immune response to a cell presenting GABRA2 polypeptide on its cell surface.

Hence, according to specific embodiments, the agent is capable of eliciting an immune response against a cell expressing GABRA2.

As used herein, the phrase "eliciting an immune response" refers to stimulation of an immune cell (e.g. T cell, dendritic cell, NK cell, B cell) that results in cellular proliferation, maturation, cytokine production and/or induction of regulatory or effector functions.

According to specific embodiments, the immune response comprises a T cell response.

According to specific embodiments, the immune response comprises a dendritic cell response.

According to specific embodiments, the immune response is specific to a cell expressing GABRA2 with no cross reactivity with a cell not expressing GABRA2.

Methods of evaluating immune cell activation or function are well known in the art and include, but are not limited to, proliferation assays such as BRDU and thymidine incorporation, cytotoxicity assays such as chromium release, cytokine secretion assays such as intracellular cytokine staining ELISPOT and ELISA, expression of activation markers such as CD25, CD69 and HLADR using flow cytometry and multimer (e.g. tetramer) assays.

According to some embodiments, the therapeutic or detectable moieties are conjugated by translationally fusing the polynucleotide encoding the agent disclosed herein with the nucleic acid sequence encoding the therapeutic or detectable moiety.

Additionally or alternatively, the therapeutic or detectable moieties can be chemically conjugated (coupled) to the agent disclosed herein, using any conjugation method known to one skilled in the art. For example, a peptide can be conjugated to an agent of interest, using a 3-(2-pyridyldithio)propionic acid Nhydroxysuccinimide ester (also called N-succinimidyl 3-(2-pyridyldithio) propionate) ("SDPD") (Sigma, Cat. No. P-3415; see e.g., Cumber et al. 1985, Methods of Enzymology 112: 207-224), a glutaraldehyde conjugation procedure (see e.g., G. T. Hermanson 1996, "Antibody Modification and Conjugation, in Bioconjugate Techniques, Academic Press, San Diego) or a carbodiimide conjugation procedure [see e.g., J. March, Advanced Organic Chemistry: Reaction's, Mechanism, and Structure, pp. 349-50 & 372-74 (3d ed.), 1985; B. Neises et al. 1978, Angew Chem., Int. Ed. Engl. 17:522; A. Hassner et al. 1978, Tetrahedron Lett. 4475; E. P. Boden et al. 1986, J. Org. Chem. 50:2394 and L. J. Mathias 1979, Synthesis 561].

A therapeutic or detectable moiety can be attached, for example, to the antibody of some embodiments of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling of antibodies is provided in details in U.S. Pat. Nos. 3,940,475, 4,289,747, and 4,376,110.

The agent can also be attached to particles which comprise the therapeutic or detectable moiety (e.g. cytotoxic agent). Methods of covalently binding an agent (e.g. antibody) to an encapsulating particle are known in the art and disclosed for example in U.S. Pat. Nos. 5,171,578, 5,204,096 and 5,258,499.

Any of the peptides and proteinaceous agents described herein can be encoded from a polynucleotide. These polynucleotides can be used as therapeutics per se or in the recombinant production of the peptide and/or agent.

Thus, according to an aspect of the present invention there is provided an isolated polynucleotide comprising a nucleic acid sequence encoding the agent of some embodiments of the invention. According to an aspect of the present invention there is provided an isolated polynucleotide comprising a nucleic acid sequence encoding the antibody of some embodiments of the invention.

Non-limiting Examples of nucleic acid sequences encoding the light chain, the heavy chain, the CDRs and variable regions that make up an antibody that can be used with some embodiments of the present invention are provided in SEQ ID NO: 1-5 and 11-15.

Thus, according to specific embodiments, the polynucleotide comprises a nucleic acid sequence having at least 80%, at least 85%, at least 90%, at least 95%, at least 97%, at least 98%, at least 99% or 100% identity to a nucleic acid sequence selected from the group consisting of SEQ ID NO: 1-5 and 11-15, each possibility represents a separate embodiment of the present invention.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

To express exogenous peptide or agent in mammalian cells, a polynucleotide sequence encoding the peptide and/or the agent is preferably ligated into a nucleic acid construct suitable for mammalian cell expression.

Thus, according to an aspect of the present invention there is provided a nucleic acid construct comprising the isolated polynucleotide.

Such a nucleic acid construct or system includes at least one cis-acting regulatory element for directing expression of the nucleic acid sequence. Cis-acting regulatory sequences include those that direct constitutive expression of a nucleotide sequence as well as those that direct inducible expression of the nucleotide sequence only under certain conditions. Thus, for example, a promoter sequence for directing transcription of the polynucleotide sequence in the cell in a constitutive or inducible manner is included in the nucleic acid construct.

Also provided are cells which comprise the polynucleotides/expression vectors as described herein.

Such cells are typically selected for high expression of recombinant proteins (e.g., bacterial, plant or eukaryotic cells e.g., CHO, HEK-293 cells), but may also be an immune cell (e.g., macrophages, dendritic cells, T cells, B cells or NK cells) when for instance the CDRs of the agent are implanted in a T Cell Receptor or CAR transduced in said cells which are used in adoptive cell therapy.

Also provided hybrodima cells expressing antibodies of some embodiments of the invention (e.g., 10C5B9).

The agents (e.g. antibody) of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the component accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

According to specific embodiments, the agent is not delivered to the CNS.

According to specific embodiments, the agent cannot cross or formulated such that it cannot cross the BBB.

Alternately, one may administer the pharmaceutical composition in a local rather than systemic manner, for example, via injection of the pharmaceutical composition directly into a tissue region of a patient.

Pharmaceutical compositions of some embodiments of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments the present invention may also be formulated in rectal compositions such as suppositories or retention enemas, using, e.g., conventional suppository bases such as cocoa butter or other glycerides.

Pharmaceutical compositions suitable for use in context of some embodiments of the present invention include compositions wherein the active ingredients are contained in an amount effective to achieve the intended purpose. More specifically, a therapeutically effective amount means an amount of active ingredients effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods disclosed herein, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

It will be appreciated that the therapeutic agents disclosed herein can be provided to the individual in combination with additional active agents to achieve an improved therapeutic effect as compared to treatment with each agent by itself.

Thus, according to specific embodiments, the agent can be administered to a subject in combination with other established or experimental therapeutic regimen to treat cancer including analgesics, chemotherapy, radiotherapy, phototherapy and photodynamic therapy, surgery, nutritional therapy, ablative therapy, combined radiotherapy and chemotherapy, brachitherapy, proton beam therapy, immunotherapy, cellular therapy, photon beam radiosurgical therapy and other treatment regimens which are well known in the art.

According to specific embodiments the agent is administered to a subject in combination with a cancer therapy.

Non-limiting Examples of cancer therapies that can be used with specific embodiments of the invention are described in details hereinbelow.

In such therapy, measures (e.g., dosing and selection of the complementary agent) are taken to adverse side effects which may be associated with combination therapies.

Administration of such combination therapy can be simultaneous, such as in a single capsule having a fixed ratio of these active agents, or in multiple capsules for each agent.

According to specific embodiments, treatment does not comprise an immunosuppressive drug.

According to specific embodiments, treatment does not comprise a TRL9 agonist or inhibitors of the mammalian target of Rapamycin (mTOR) pathway (e.g. Rapamycin).

According to specific embodiments, treatment does not Boroproline or the agent of Formula I described in US Patent Application Publication No. 20050084490.

According to specific embodiments, treatment consists of the agent disclosed herein.

According to specific embodiments, treatment consists of the antibody disclosed herein.

Compositions of some embodiments of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to an aspect of the present invention, there is provided an article of manufacture comprising a cancer therapy and an agent capable of:
  (i) specifically binding GABRA2, the agent comprising a therapeutic moiety; and/or
  (ii) downregulating activity and/or expression of said GABRA2.

According to an aspect of the present invention, there is provided an article of manufacture comprising a cancer therapy and an antibody comprising an antigen recognition domain which specifically binds GABRA2 and comprises CDRs as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody.

According to specific embodiments, the article of manufacture is identified for the treatment of cancer.

As GABRA2 has been identified as a CSC marker by the present inventors, specific embodiments of the present invention further propose analyzing for the presence and/or level of GABRA2 for the purpose of diagnosis, staging, monitoring treatment efficacy and/or selecting treatment regime.

Thus, according to an aspect of the present invention, there is provided a method of diagnosing cancer in a subject, the method comprising determining a level of GABRA2 in a biological sample of the subject, wherein said level of said GABRA2 above a predetermined threshold is indicative of cancer.

As used herein the term "diagnosing" refers to determining presence or absence of a pathology (i.e. cancer), classifying a pathology or a symptom, determining a severity of the pathology (e.g. grade or stage), monitoring pathology progression, forecasting an outcome of a pathology and/or prospects of recovery and screening of a subject for a specific disease.

The methods of some embodiments of the invention are particularly useful in detecting the early stages of cancer in outwardly healthy individuals.

According to some embodiments, the presence of GABRA2 (i.e. irrespective of its level) is indicative of the cancer.

According to some embodiments the level of GABRA2 is indicative of the cancer.

According to some embodiments, the level of GABRA2 is indicative of cancer prognosis.

According to specific embodiments, a level above a predetermined threshold of GABRA2 is indicative of cancer.

As mentioned, the methods of some embodiments of the present invention comprise determining a level of GABRA2 in a biological sample of the subject.

Such biological samples include but are not limited to, a cell obtained from any tissue biopsy, a tissue, an organ, a blood cell, a bone marrow cell, body fluids such as blood, saliva, spinal fluid, lymph fluid, rinse fluid that may have been in contact with the tumor, the external sections of the skin, respiratory, intestinal, and genitourinary tracts, urine and feces.

According to specific embodiments, the biological sample is selected from the group consisting of urine, blood, serum, lymph fluid, feces and rinse fluid that was in contact with a tumor.

According to specific embodiments, the biological sample comprises cells.

According to specific embodiments, the biological sample comprises cancerous cells.

According to specific embodiments, the biological sample is a sample of the tumor.

According to specific embodiments, the sample is a primary tumor sample.

According to specific embodiments, the method disclosed herein comprises obtaining the biological sample prior to the determining.

Hence, according to specific embodiments, the determining is effected in-vitro or ex-vivo.

The biological sample can be obtained using methods known in the art such as using a syringe with a needle, a scalpel, fine needle biopsy, needle biopsy, core needle biopsy, fine needle aspiration (FNA), surgical biopsy, buccal smear, lavage and the like. According to specific embodiments, the biological sample is obtained by biopsy. According to specific embodiments, the level of GABRA2 is determined in a cell comprised in the biological sample.

It will be appreciated that a specific cell type may be further isolated from the biological sample obtained from the subject. Methods of isolating specific cell types are well known in the art including, but not limited to, density gradient centrifugation, flow cytometry and magnetic beads separation.

As used herein the phrase "predetermined threshold" refers to a level of GABRA2 that characterizes a healthy sample of the same origin assayed under the same conditions. Such a level can be experimentally determined by comparing samples with normal levels of GABRA2 (e.g., samples obtained from healthy subjects e.g., not having cancer) to samples derived from subjects diagnosed with cancer. Alternatively, such a level can be obtained from the scientific literature and from databases.

According to specific embodiments, the predetermined threshold is derived from a control sample.

Several control samples can be used with specific embodiments of the present invention. Typically, the control sample contains a level of GABRA2 comparable to a healthy biological sample.

Since biological characteristics depend on, amongst other things, species and age, it is preferable that the control sample is obtained from a subject of the same species, age, gender and from the same sub-population (e.g. smoker/nonsmoker).

According to specific embodiments, the control sample comprises a biological sample of the same type as the biological sample of the subject.

According to specific embodiments, the control sample is a healthy control sample.

According to specific embodiments, the control sample is a non-cancerous tissue of said subject.

According to specific embodiments, the control sample is a cancerous cell with a level of GABRA2 similar to levels of same in a healthy cell of the same type.

According to specific embodiments, the control sample is obtained from the scientific literature or from a database, such as the known age matched mean value in a non-cancerous population.

According to specific embodiments, the increase/decrease above or below a predetermined threshold is statistically significant.

According to specific embodiments, the predetermined threshold is at least 1.5 fold, at least 2 fold, at least 3 fold, at least 5 fold, at least 10 fold, or at least 20 fold as compared the level of GABRA2 in a control sample as measured using the same assay such as any RNA (e.g. PCR, Northern blot) and/or protein (e.g. western blot, flow cytometry) assay suitable for measuring expression level of a target, as further disclosed herein.

According to specific embodiments, the predetermined threshold is at least 1.5 fold as compared the level of GABRA2 in a control sample.

According to specific embodiments, the predetermined threshold is at least 2%, at least 5%, at least 10%, at least 20%, at least 30%, at least 40%, at least 50%, at least 60%, at least 70%, at least 80%, at least 90%, e.g., 100%, at least 200%, at least 300%, at least 400%, at least 500%, at least 600% as compared the level of GABRA2 in a control sample.

Determining the level of GABRA2 can be affected by any method known in the art, such as but not limited to PCR, RNA chip, Western blot, ELISA, flow cytometry.

As used herein, the phrase "level" when relating to GABRA2 refers to the degree of gene expression (e.g. mRNA or protein).

It should be noted that the expression level can be determined in arbitrary absolute units, or in normalized units (relative to known expression levels of a control sample). For example, when using RNA chips, the expression levels are normalized according to internal controls or by using quantile normalization.

Expression level can be determined in the biological sample using any structural, biological or biochemical method which is known in the art for detecting the expression level at the transcript or the protein level.

According to specific embodiments, the RNA or the protein molecules are extracted from the biological sample of the subject. Thus, according to specific embodiments, the method further comprises extracting RNA or a protein from the biological sample prior to the determining.

Methods of extracting RNA or protein molecules from biological samples are well known in the art. The extracted RNA can be further processed to a cDNA. Methods of and commercially available kits for converting RNA to cDNA are well known in the art and include e.g. the use of the enzyme reverse transcriptase. Once obtained, the RNA, cDNA or protein molecules can be characterized for the level of various RNA, cDNA and/or protein molecules using methods known in the arts.

According to specific embodiment, determining the level of GABRA2 is effected at the transcript level using RNA or DNA detection methods.

Thus, according to some embodiments, detection of the level of GABRA2 is performed by contacting the biological sample, the tissue, the cell, or fractions or extracts thereof with a probe (e.g. oligonucleotide probe or primer) which specifically hybridizes to a GABRA2 polynucleotide. Such a probe can be at any size, such as a short polynucleotide (e.g., of 15-200 bases), an intermediate polynucleotide of 100-2000 bases and a long polynucleotide of more than 2000 bases.

The probe used by the present invention can be any directly or indirectly labeled RNA molecule [e.g., RNA oligonucleotide (e.g., of 17-50 bases), an in-vitro transcribed RNA molecule], DNA molecule (e.g., oligonucleotide, e.g., 15-50 bases, cDNA molecule, genomic molecule) and/or an analogue thereof [e.g., peptide nucleic acid (PNA)] which is specific to GABRA2 RNA transcript. According to specific embodiments, the probe is bound to a detectable moiety.

Oligonucleotides designed according to the teachings of the present invention can be generated according to any oligonucleotide synthesis method known in the art such as enzymatic synthesis or solid phase synthesis.

According to specific embodiments, the contacting is effected under conditions which allow the formation of a complex comprising GABRA2 mRNA or cDNA present in the cell and the probe. The complex can be formed at a variety of temperatures, salt concentration and pH values which may vary depending on the method and the biological sample used and those of skills in the art are capable of adjusting the conditions suitable for the formation of each nucleotide/probe complex.

Thus, according to an aspect of the present invention there is provided a composition of matter comprising a biological sample of a subject (or an RNA extracted from a biological sample of a subject) diagnosed with cancer and a probe capable of detecting a GABRA2 polynucleotide.

According to another aspect of the present invention there is provided an article of manufacture comprising a biological sample of a subject (or an RNA extracted from a biological sample of a subject) diagnosed with cancer, and in a separate container a probe capable of detecting a GABRA2 polynucleotide.

According to specific embodiments, the composition or the article of manufacture does not comprise more than 10 probes capable of detecting 10 distinct markers. According to specific embodiments, the composition or the article of manufacture does not comprise more than 5 probes capable of detecting 5 distinct markers. According to specific embodiments, the composition or the article of manufacture comprises only probes capable of detecting GABRA2. According to specific embodiments, the composition or the article of manufacture comprises a single probe.

According to specific embodiments, the composition or the article of manufacture further comprises an RNase inhibitor.

Non-limiting examples of methods of detecting RNA and/or cDNA molecules in a sample include Northern blot analysis, RT-PCR [e.g., a semi-quantitative RT-PCR, quantitative RT-PCR using e.g., the Light Cyclerm (Roche)], RNA in-situ hybridization (using e.g., DNA or RNA probes to hybridize RNA molecules present in the cells or tissue sections), in-situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface [e.g., a glass wafer) with addressable location, such as Affymetrix microarray (Affymetrix®, Santa Clara, CA)].

As mentioned, according to specific embodiments, determining the level of GABRA2 is effected at the protein level using protein detection methods.

Examples of agents capable of binding the peptides and/or detecting the peptide, such as antibodies, are described in details hereinabove.

Thus, according to some embodiments, detection of the level of the GABRA2 protein is performed by contacting the biological sample, the tissue, the cell, or fractions or extracts thereof with an antibody which specifically binds to GABRA2. According to specific embodiments, the contacting is effected under conditions which allow the formation of a complex comprising GABRA2 present in the biological sample and the antibody (i.e. immunocomplex).

The immunocomplex can be formed at a variety of temperatures, salt concentration and pH values which may vary depending on the method and the biological sample used and those of skills in the art are capable of adjusting the conditions suitable for the formation of each immunocomplex.

Thus, according to an aspect of the present invention there is provided a composition of matter comprising a biological sample of a subject (or a lysate of a biological sample of a subject) diagnosed with cancer, and an antibody capable of detecting GABRA2.

According to an aspect of the present invention there is provided a composition of matter comprising a biological sample of a subject (or a lysate of a biological sample of a subject) diagnosed with cancer, and an antibody comprising an antigen recognition domain which specifically binds GABRA2 and comprises CDRs as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody.

According to an aspect of the present invention there is provided an article of manufacture comprising a biological sample of a subject (or a lysate of a biological sample of a subject) diagnosed with cancer, and in a separate container an antibody capable of detecting GABRA2.

According to an aspect of the present invention there is provided an article of manufacture comprising a biological sample of a subject (or a lysate of a biological sample of a subject) diagnosed with cancer, and in a separate container an antibody comprising an antigen recognition domain which specifically binds GABRA2 and comprises CDRs as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody.

According to a specific embodiment, the composition or the article of manufacture further comprises a secondary antibody capable of binding the antibody.

According to specific embodiments, the composition further comprises a protease inhibitor.

Non-limiting examples of methods of detecting the level of specific protein molecules in a sample include Enzyme linked immunosorbent assay (ELISA), Western blot analysis, immunoprecipitation (IP), radio-immunoassay (RIA), Fluorescence activated cell sorting (FACS), immunohistochemical analysis, in-situ activity assay (using e.g., a chromogenic substrate applied on the cells containing an active enzyme), in-vitro activity assays (in which the activity of a particular enzyme is measured in a protein mixture extracted from the cells) and molecular weight-based approach.

The antibody or probe used by the present invention can be any directly or indirectly labeled antibody or probe. According to specific embodiments, the antibody or probe is bound to a detectable moiety. Non-limiting examples of detectable moieties and methods of detection are described in details hereinabove. According to a specific embodiment, the detection is effected by FACS.

According to specific embodiments, the methods disclosed herein comprise corroborating the diagnosis using a state of the art technique.

Such methods are known in the art and depend on the cancer type and include, but not limited to, complete blood count (CBC), tumor marked tests (also known as biomarkers), imaging (such as MRI, CT scan, PET-CT, ultrasound, mammography and bone scan), endoscopy, colonoscopy, biopsy and bone marrow aspiration.

According to specific embodiments the diagnostic method further comprises treating the diagnosed subject with an effective amount of a cancer therapy.

Thus, according to an aspect of the present invention, there is provided a method of treating cancer in a subject in need thereof, the method comprising:
(a) diagnosing the subject according to the method disclosed herein; and wherein when said level of said GABRA2 above a predetermined threshold is indicated,
(b) selecting a cancer therapy based on the level of said GABRA2,
thereby treating the cancer.

According to another aspect of the present invention, there is provided a method of treating cancer in a subject in need thereof, the method comprising:
(a) diagnosing the subject according to the method disclosed herein; and wherein when said level of said GABRA2 above a predetermined threshold is indicated,
(b) treating said subject with a cancer therapy,
thereby treating the cancer.

As used herein, the phrase "cancer therapy" refers to any established or experimental therapeutic regimen that has an anti-tumor effect including analgesics, chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy, photon beam radiosurgical therapy and other treatment regimens which are well known in the art.

As GABRA2 was identified by the present inventors as a CSC marker, its expression level can be used for cancer prognosis. Hence, according to specific embodiments, the cancer therapy is selected based on the prognosis of the cancer. That is, a cancer with poor prognosis is treated with a treatment regime suitable for poor prognosis according to e.g. established protocols; while cancer with good prognosis is treated with a treatment regime suitable for good prognosis according to other e.g. established protocols.

According to specific embodiments, the level of GABRA2 can indicate the likelihood that the cancer will respond to the given cancer therapy (personalized medicine). Hence, according to specific embodiments, the cancer therapy is selected based on the levels of GABRA2.

The cancer therapy used with specific embodiments of the present invention include chemotherapy, small molecules, biological drugs, hormonal therapy, antibodies and targeted therapy.

According to specific embodiments, the cancer therapy is selected from the group consisting of radiation therapy, chemotherapy and immunotherapy.

Anti-cancer drugs that can be used with specific embodiments of the invention include, but are not limited to. Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Non-limiting examples for anti-cancer approved drugs include: abarelix, aldesleukin, aldesleukin, alemtuzumab, alitretinoin, allopurinol, altretamine, amifostine, anastrozole, arsenic trioxide, asparaginase, azacitidine, AZD9291, AZD4547, AZD2281, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dabrafenib, dacarbazine, dactinomycin, actinomycin D, Darbepoetin alfa, Darbepoetin alfa, daunorubicin liposomal, daunorubicin, decitabine, Denileukin diftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolone phenpropionate, nelarabine, Nofetumomab, Oprelvekin, Oprelvekin, oxaliplatin, paclitaxel, palbociclib palifermin, pamidronate, pegademase, pegaspargase, Pegfilgrastim, pemetrexed disodium, pentostatin, pipobroman, plicamycin mithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trametinib, Trastuzumab, tretinoin ATRA, Uracil Mustard, valrubicin, vinblastine, vinorelbine, zoledronate and zoledronic acid.

According to specific embodiments, the anti-cancer drug is selected from the group consisting of Gefitinib, Lapatinib, Afatinib, BGJ398, CH5183284, Linsitinib, PHA665752, Crizotinib, Sunitinib, Pazopanib, Imatinib, Ruxolitinib, Dasatinib, BEZ235, Pictilisib, Everolimus, MK-2206, Trametinib/AZD6244, Vemurafinib/Dabrafenib, CCT196969/CCT241161, Barasertib, VX-680, Nutlin3, Palbociclib, BI 2536, Bardoxolone, Vorinostat, Navitoclax (ABT263), Bortezomib, Vismodegib, Olaparib (AZD2281), Simvastatin, 5-Fluorouricil, Irinotecan, Epirubicin, Cisplatin and Oxaliplatin.

According to specific embodiments, the cancer therapy does not comprise an immunosuppressive drug.

According to specific embodiments, the cancer therapy does not comprise a TRL9 agonist or inhibitors of the mammalian target of Rapamycin (mTOR) pathway (e.g. Rapamycin).

According to specific embodiments, the cancer therapy does not Boroproline or the agent of Formula I described in US Patent Application Publication No. 20050084490.

According to specific embodiments, the cancer therapy comprises the agents disclosed herein.

Hence, according to specific embodiments, the cancer therapy comprises an agent capable of:
  (i) specifically binding said GABRA2, the agent comprising a therapeutic moiety; and/or
  (ii) downregulating activity and/or expression of said GABRA2.

According to specific embodiments, the cancer therapy consists of an agent capable of:
  (i) specifically binding said GABRA2, the agent comprising a therapeutic moiety; and/or
  (ii) downregulating activity and/or expression of said GABRA2.

According to specific embodiments, the cancer therapy comprises an antibody comprising an antigen recognition domain which specifically binds GABRA2 and comprises CDRs as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody.

According to specific embodiments, the cancer therapy consists of an antibody comprising an antigen recognition domain which specifically binds GABRA2 and comprises CDRs as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody.

According to an aspect of the present invention, there is provided a method of treating cancer in a subject in need thereof, the method comprising:
  (a) diagnosing the subject according to the method disclosed herein; and wherein when said level of said GABRA2 above a predetermined threshold is indicated,
  (b) administering to said subject an effective amount of an agent capable of:
    (i) specifically binding said GABRA2, the agent comprising a therapeutic moiety; and/or
    (ii) downregulating activity and/or expression of said GABRA2,
  thereby treating the cancer.

According to an additional or an alternative aspect of the invention, there is provided a method of treating cancer in a subject in need thereof, the method comprising:
  (a) diagnosing the subject according to the method disclosed herein; and wherein when said level of said GABRA2 above a predetermined threshold is indicated,
  (b) administering to said subject an effective amount of an antibody comprising an antigen recognition domain which specifically binds GABRA2 and comprises CDRs as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of the antibody,
  thereby treating the cancer.

It will be appreciated that the identification of CSCs has a variety of applications pertaining to individually optimizing a treatment for cancer, monitoring cancer treatment in a subject, determining a cancer therapy for a subject, predicting efficacy of a cancer therapy and identifying an agent capable of treating the cancer.

Thus, according to an aspect of the present invention there is provided a method of monitoring efficacy of cancer therapy in a subject, the method comprising determining a level of GABRA2 in a biological sample of the subject following the cancer therapy, wherein a decrease from a predetermined threshold in the level of said GABRA2 following the cancer therapy indicates efficaciousness of the cancer therapy.

Thus, a decrease in the level of GABRA2 is indicative of the cancer therapy being efficient. According to specific embodiments, the decrease in the level of GABRA2 is indicative of reduction of CSCs.

On the other hand, if there is no change in the level of GABRA2, or in case there is an increase in the level of GABRA2, then the cancer therapy is not efficient in treating the cancer and additional and/or alternative therapies (e.g., treatment regimens) may be used. According to specific embodiments, no change in the level of GABRA2, or in case there is an increase in the level of GABRA2, indicates the cancer therapy is not efficient in eliminating (e.g., killing, depleting) the CSCs from the treated subject.

According to specific embodiments of the monitoring aspects disclosed herein, the predetermined threshold is in comparison to the level in the subject prior to cancer therapy.

According to specific embodiments of the monitoring aspects disclosed herein, the predetermined threshold is at least 1.5 fold, at least 2 fold, at least 3 fold, at least 5 fold, at least 10 fold, or at least 20 fold as compared the level of GABRA2 in a control sample or in the subject prior to the cancer therapy as measured using the same assay such as any RNA (e.g. PCR, Northern blot) or protein (e.g. western blot, flow cytometry) assay suitable for measuring level of a target, as further disclosed herein.

According to a specific embodiment, the predetermined threshold is at least 1.5 fold as compared the level of GABRA2 in a control sample or in the subject prior to the cancer therapy.

According to specific embodiments, the predetermined threshold is at least 2%, at least 5%, at least 10%, at least 20%, at least 30%, at least 40%, at least 50%, at least 60%, at least 70%, at least 80%, at least 90%, e.g., 100%, at least 200%, at least 300%, at least 400%, at least 500%, at least 600% as compared the level of GABRA2 in a control sample or in the subject prior to the cancer therapy.

According to other specific embodiments of this aspect of the present invention, the predetermined threshold can be determined in a subset of subjects with known outcome of cancer therapy.

According to another aspect of the present invention, there is provided a method of predicting an efficacy of a cancer therapy for treatment of a subject, the method comprising:

(a) contacting a biological sample of the subject with a therapeutically effective amount of the cancer therapy; and (b) determining a level of GABRA2 in said biological sample of said subject following said contacting with said cancer therapy;

wherein a decreased level of expression of said GABRA2 following said contacting with said cancer therapy relative to a level of expression of said GABRA2 prior to said contacting with said cancer therapy indicates that the cancer therapy is efficient for treating the subject, thereby predicting efficacy of the cancer therapy.

According to specific embodiments of this aspect of the present invention, the method comprising determining a level of GABRA2 prior to the contacting.

Thus, a decrease in the level of GABRA2 is indicative of the potential cancer therapy being efficient. On the other hand, if there is no change in the level of GABRA2, or in case there is an increase in the level of GABRA2, then the potential cancer therapy is not efficient for treating the subject. According to specific embodiments, no change in the level of GABRA2, or in case there is an increase in the level of GABRA2, indicates the potential cancer therapy is not efficient in eliminating (e.g., killing, depleting) the CSCs from the treated subject.

According to specific embodiments, the decrease in the level of GABRA2 following the contacting compared to the level of GABRA2 prior to the contacting is statistically significant.

According to specific embodiments, the decrease in the level of GABRA2 following the contacting is at least 1.5 fold, at least 2 fold, at least 3 fold, at least 5 fold, at least 10 fold, or at least 20 fold as compared the level of GABRA2 prior to the contacting as measured using the same assay such as any RNA (e.g. PCR, Northern blot) and/or protein (e.g. western blot, flow cytometry) assay suitable for measuring expression level of a target, as further disclosed herein.

According to a specific embodiment, the decrease in the level of GABRA2 following the contacting is at least 1.5 fold as compared the level of GABRA2 prior to the contacting.

According to specific embodiments, the decrease in the level of GABRA2 following the contacting is at least 2%, at least 5%, at least 10%, at least 20%, at least 30%, at least 40%, at least 50%, at least 60%, at least 70%, at least 80%, at least 90%, e.g., 100%, at least 200%, at least 300%, at least 400%, at least 500%, at least 600% as compared the level of GABRA2 prior to the contacting.

As used herein the term "contacting" refers to the positioning of the cancer therapy such that it is in direct or indirect contact with a biological sample expressing GABRA2. According to specific embodiments, the cancer therapy is contacted with the biological sample for a period long enough to have an anti-cancer effect.

According to specific embodiments, the contacting is effected ex-vivo or in-vitro.

It will be appreciated that as GABRA2 has been identified by the present inventors as a CSC marker, the present invention further envisages the use of this marker for the isolation of CSCs. Contemplated methods include centrifugation based methods, elutriation, density gradient separation, apheresis, affinity selection, panning, immunological-based systems such as fluorescence activated cell sorting (FACS); immunoaffinity exchange; non-optical cell sorting methods including magnetic cell sorting using antibody-coated magnetic particles that bind to a specific cell type to separate desired cells.

It is expected that during the life of a patent maturing from this application many relevant agents that specifically bind and/or downregulate expression or activity of GABRA2 will be developed and the scope of the term agent is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

In vivo xenograft formadon—Primary human malignant rhabdoid tumor (MRT) samples were obtained from patients within 1 hour of surgery. Informed consent was given by the legal guardians of the patients involved according to the declaration of Helsinki. Tumor xenografts (Xn) were formed by subcutaneous transplantations of 2-5 mm tumor pieces into 5- to 8-week-old, female, nonobese diabetic severe combined immunodeficient (NOD-SCID) mice (FIG. 1). The animal experiments were performed in accordance with the Guidelines for Animal Experiments of Sheba Medical Center. For each experiment, tumor-bearing mice were randomly assigned to the different treatment groups just prior to initiation of treatment. The mice were anesthetized for all procedures and sacrificed at the end of each experiment. All data from animals that died or had to be sacrificed prior to the scheduled termination of the experiment were excluded. Mice were maintained in a pathogen-free environment and monitored weekly for tumor growth. Secondary tumors were detected by palpation every week. The patient derived Xns (PDX) were harvested approximately 1-3 months post implantation or when they reached a size of 1.5 cm diameter. Time to engraftment, time to resection, weight and volume for each engrafted Xn were recorded. Xn tissue was immediately cut into small pieces and processed for further experiments as follows: (i) flash freezing for subsequent molecular characterization of extracted analyses; (ii) formalin fixation and paraffin embedding for future immunohistochemical (IHC) studies; (iii) tissue implantation subcutaneously into the flank of NOD-SCID mice; and (iv) preparation of single cell suspensions as described below for subsequent Xn propagation and in-vitro experiments (e.g. in-vitro studies, limiting dilution assays, FACS analysis, FACS sorting, immunohistochemistry and in-vivo studies as described in International Patent Application Publication no. WO2015/198334). Single cells suspensions were obtained by mincing the samples in Iscove's modification of Dulbecco's medium (IMDM) containing antibiotics (penicillin and streptomycin), followed by treatment with collagenase IV for 2h at 37° C. Enzymatically treated tissue was triturated using IMDM at twice the volume of the collagenase solution and the suspension filtered (100 μm cell strainer) and washed twice with IMDM containing antibiotics. Erythrocytes were removed by ACK RBS lysis buffer.

Xn serial passages were formed using two methods: 1. injection of approximately $1 \times 10^6$ dissociated cells from freshly retrieved Xn; Cells were injected in 100 μl 1:1 serum free medium/Matrigel (BD Biosciences, San Jose, CA). 2. Xn tissue was cut into 2-5 mm pieces and implanted subcutaneously in the back of the mouse.

Serial propagation allowed to establish early-(<P5), intermediate-(P5-P10) and late-passage (P10-P16) PDX that were studied for CSCs phenotype characterization and elucidation of pathogenic pathways associated with tumor-initiating capacity. Tumor growth was followed by measuring perpendicular diameters of the tumors with a Vernier caliper. Tumor volume was calculated using the equation ½(Length×Width²). In addition, tumors were excised postmortem, weighed and processed for further experiments as described. Only tumors that could be excised completely without additional invaded tissue were used for weight measurements.

Fluorescence-activated cell sorting (FACS)—FACS sorting based on ALDH1 activity was performed on MRT cells using the ALDEFLUOR kit (StemCell Technologies, Durham, NC, USA) according to manufacture protocol.

RNA sequencing analysis—The RNA sequencing data was deposited in publicly library (GEO); accession numbers GSE114471. Bulk total RNA was prepared from $\sim 1.5 \times 10^5$ cells using the Direct-zol™-96 RNA Isolation kit (Zymo Research) according to the manufacturer's instructions and stored in −80° C. in nuclease free water. Total RNA was quantified on an Agilent BioAnalyzer and 1 μg of RNA was used to prepare cDNA libraries using the TruSeq mRNA-Seq library protocol (Illumina). Libraries were sequenced 1×50 bases on an Illumina HiSeq 2000 machine in two lanes. Data from the high throughput sequencing was analyzed base on the protocol by Anders et al (Anders et al., 2013).

Immunohistochemistry—Slides of Formalin-Fixed Paraffin-Embedded (FFPE) 4 μm sections obtained from nine tumor samples from brain PDX models (BN0769, BN2289, BN3733, BN2276, BN2331, BN6299, BN2287, BN2338 and BN6304) and 9 tumor samples from breast PDX models (BR0438, BRl15, BR1282, BR1283, BR5017, BR3267, BR3116, BR2014 and BR1474) were incubated with a primary anti-human-GABRA2 antibody (Abcam Cat NO. ab176170 or isotype control Rabbit IgG (Vector Cat No. I-1000) using the following conditions: Antigen retrieval: Citrate buffer, pH6.0, 100], 20 minutes, Antibody dilution; 1:50. Following wash the slides were incubated with a secondary Goat anti-Rb IgG antibody (Leica, Cat No. DS9800). All stained sections were scanned with NanoZoomer-HT 2.0 Image system for 40× magnification (Hamamatsu photonics). High resolution images for whole sections were generated and further analyzed.

Immunohistochemistry Scoring—All stained sections were scanned with NanoZoomer-HT 2.0 Image system (Hamamatsu photonics). Following an overall look at the staining pattern of each stained section a scoring standard was established based on the intensity of the staining at four levels, 0 (negative), 1 (low staining), 2 (moderate staining), 3 (strong staining). The percentages of tumor cells at different intensity levels were evaluated based on the standard, wherein the necrosis and stroma area have been excluded. Scores were presented by formula below:

$$H\text{-Score} = (\% \text{ at } 0) \times 0 + (\% \text{ at } 1) \times 1 + (\% \text{ at } 2) \times 2 + (\text{at } 3) \times 3.$$

Generation of monoclonal Hybridoma cells—5 BALB/C mice were immunized with human GABRA2 (SEQ ID NO: 21) in combination with a GS-2 adjuvant (Genscript). Following, mice were euthanized and feeder cells were collected from the abdominal cavity with 5 ml DMEM medium. The feeder cells were plated into 96-wells plates at a density of $1 \times 10^4$ cells/well, 100 μl/well. Following isolated mouse spleen cells and SP2/0 cells were mixed at a ration of 1:2.4 followed by electro fusion. Following fusion, the treated cells were plated into the 96 wells plates at a density of 50 clones/well, 100 μl/well and incubated at 5.5% CO2 for 7-10 days. An ELISA assay using plates coated with human GABRA2 (SEQ ID NO: 21) was effected to select for Hybridoma clones positive for the GABRA2 protein antigen. In the next step, subcloning through limiting dilution was effected to obtain monoclonal hybridoma cell lines: Each clone was plated into 96 wells plate at a density of 3 cells/well and cultured for 5-7 days with HT medium at 37° C., 5% CO2. An ELISA assay using plates coated with human GABRA2 (SEQ ID NO: 21) was effected to select for Hybridoma sub-clones positive for the GABRA2 protein antigen. Following the positive monoclonal cells were expanded and cryopreserved.

Antibody production—The hybridomas were cultured with DMEM medium containing 10% FBS and incubated at 37° C., 6% CO2 in humidified incubator. When the cells grew to >70% confluency, the cells were transferred to T-25 tissue culture flask containing roller bottle cell culture medium and incubated in humidified incubator at 37° C., 6% CO2; when the cells reached >70% confluency the cells were transferred to tissue culture roller bottle and incubated in an electro-thermal incubator for around 14 days. Following, the supernatant was collected, filtered with a 0.22 µm filter to remove debris and concentrated to a final volume of 100 ml and the antibody was purified using a protein A/G resin. The purified antibodies were evaluated by Western blot using Goat anti-mouse IgG (Licor Cat No. 926-32210) and tested for binding to the human GABRA2 (SEQ ID NO: 21) antigen; binding to the human GABRA2 (SEQ ID NO: 21 was also evaluated using ELISA (as described above).

Biacore analysis—Antibody was immobilized onto a CM5 sensor chip (Cat No. BR-1005-30) under 25° C. while HBS-EP was used as the running buffer. The sensor chip surface of flow cells 1 and 2 were activated by freshly mixed 50 mmol/l N-Hydroxysuccinimide (NHS) and 200 mmol/I 1-ethyl-3-(3-dimethylaminopropyl) carbodiimide hydrochloride (EDC) for 200s (10 µl/ml). Afterwards, the antibody diluted in 10 mml/l NaAC (pH 4.5) was injected into flow cell 2 to achieve conjugation of 300 Response Unit respectively, while flow cell 1 was set as blank. After the amine coupling reaction, the remaining active coupling sites on chip surface were blocked with 200s injection of 1 mol/l ethanolamine hydrochloride. The affinity assay was performed at 25° C. and the running buffer was HBS-EP. Diluted GABRA2 was injected over the surface as association phase, followed by injecting running buffer as dissociation phase. Data was processed using the Biacore 8K Evaluation software version 1.1. Flow cell 1 and blank injection of buffer in each cycle were used as double reference for Response Unit subtraction.

Antibody Sequencing—Total RNA was isolated from the hybridoma cells following the technical manual of TRIzol@ Reagent. Total RNA was then reverse-transcribed into cDNA using GenScript proprietary universal primers following the technical manual of PrimeScript™ st Strand cDNA Synthesis Kit. Antibody fragments of heavy chain and light chains were amplified using rapid amplification of cDNA ends (RACE). Amplified antibody fragments were cloned into pMD18-T vector separately to generate recombinant plasmids following the manufacturer's instructions. The plasmids were transformed into TOP10 bacteria separately and antibiotic resistant clones were selected. Colony PCR was performed to screen for clones with inserts of correct sizes. No less than 5 positive clones containing antibody fragments were sequenced by 3730 DNA Analyzer. The consensus sequence amongst the 5 clones was provided. Kabbat definition was used to determine FRs and CDRs.

Example 1

GABRA2 as a CSC Biomarker

Figure 2A:
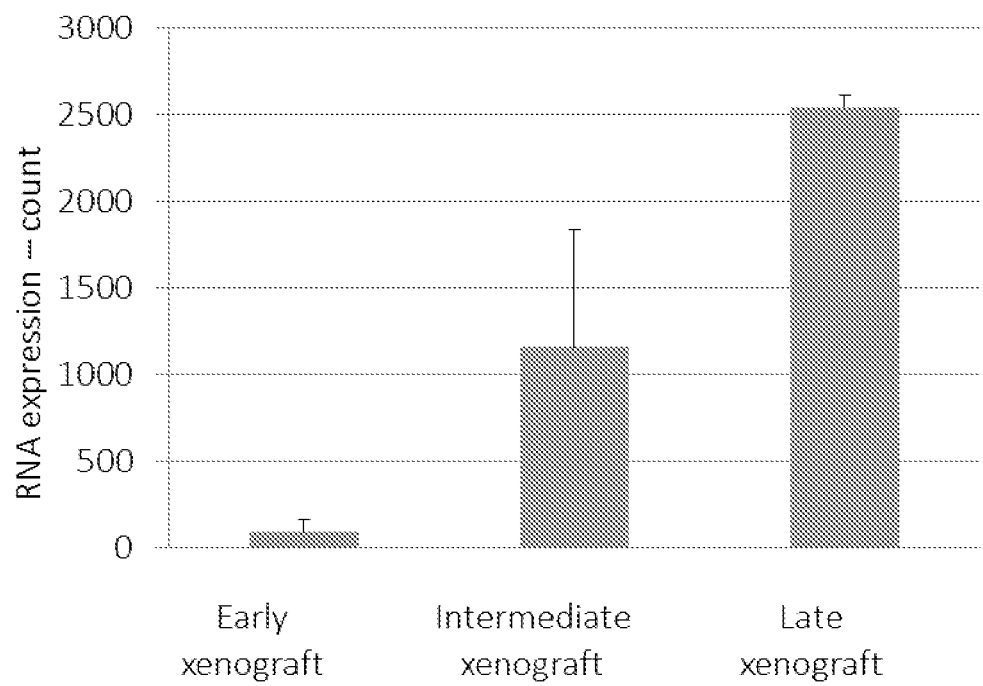
FIGS. 2A-B demonstrate an increase in GABRA2 mRNA expression levels following serial propagation of MRT PDX.
Figure 2B:
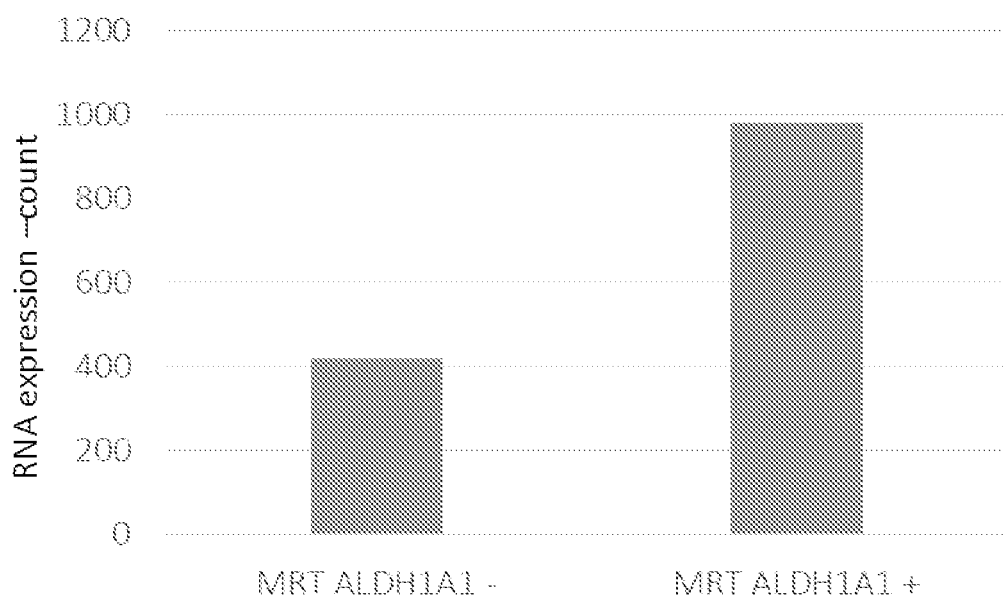
Figure 3A:
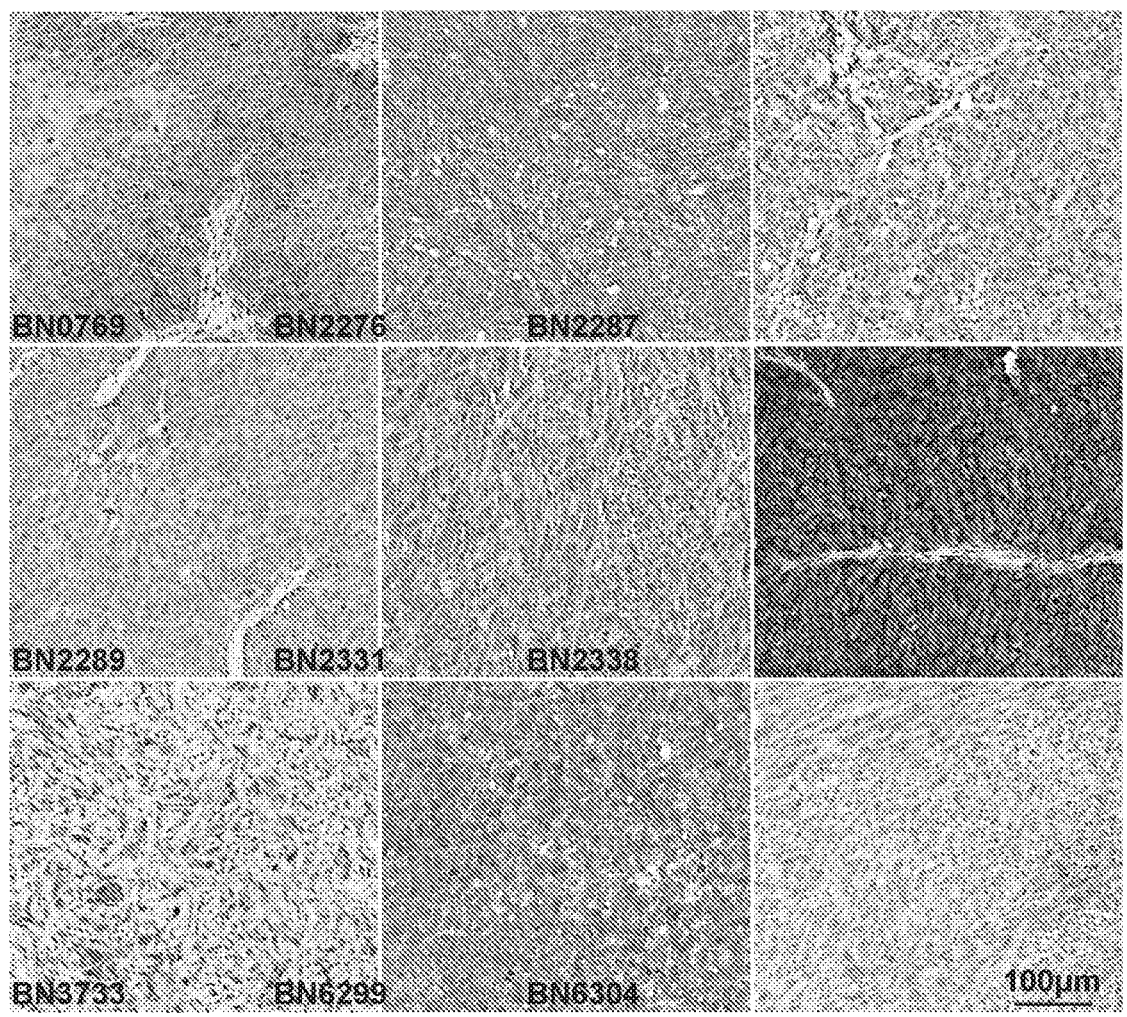
FIGS. 3A-E demonstrate expression of GABRA2 in samples of 9 brain PDX models (FIGS. 3A-B and E) and 9 breast PDX models (FIGS. 3C-D and E), as determined by immunohistochemistry with an anti-human-GABRA2 antibody (FIGS. 3A and 3C), as compared to isotype control (FIGS. 3B and 3D).
Figure 3B:
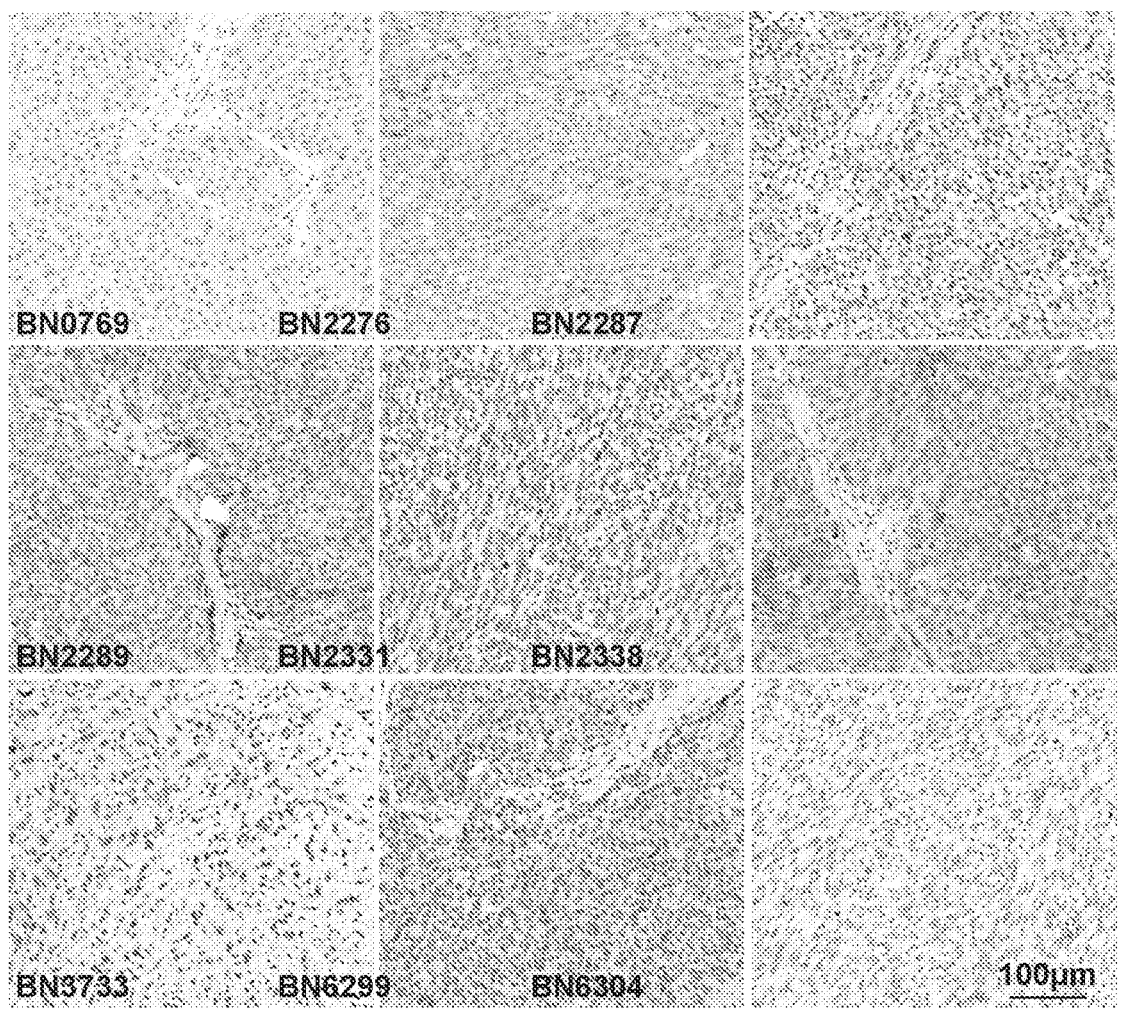
Figure 3C:
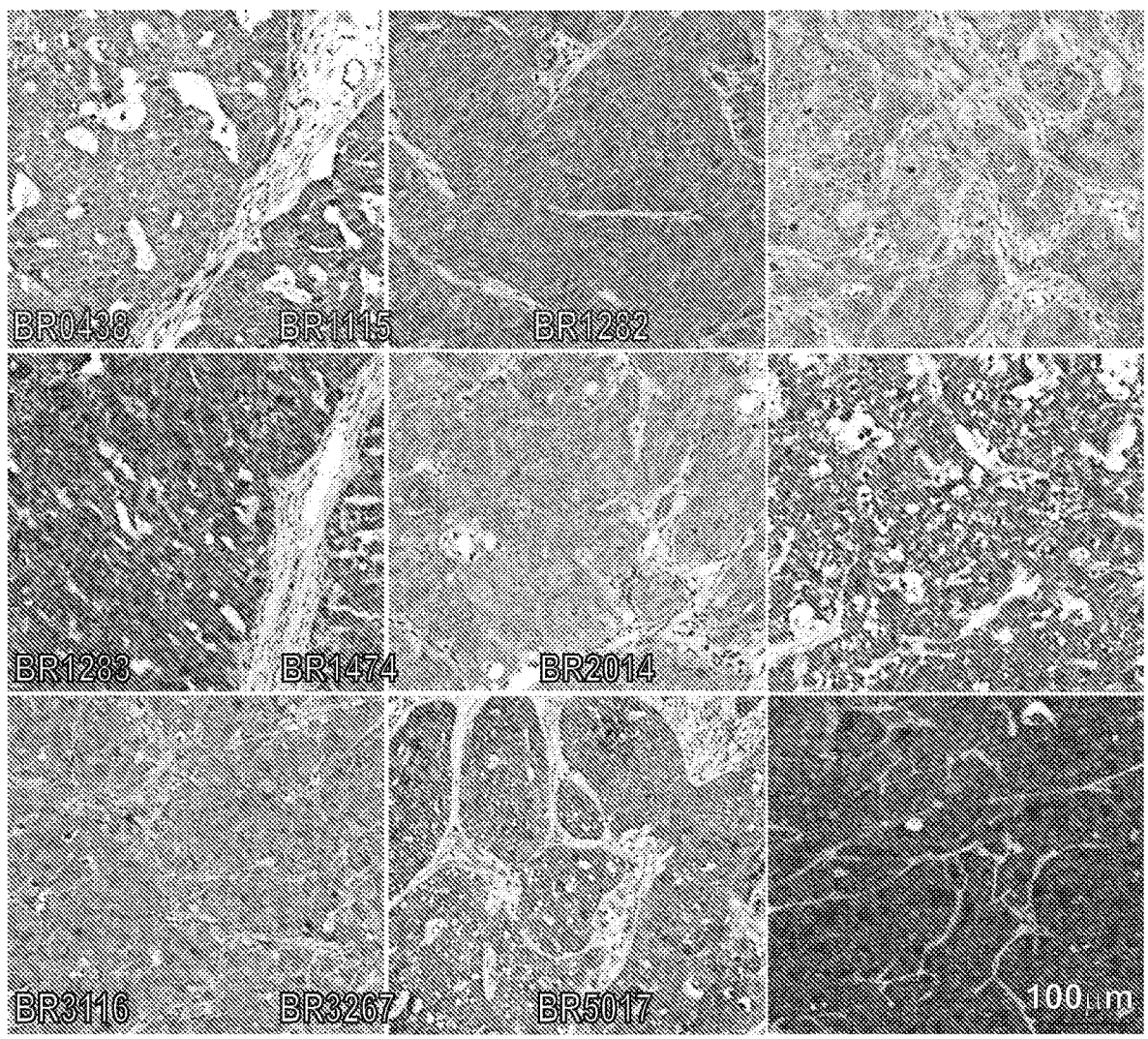
Figure 3D:
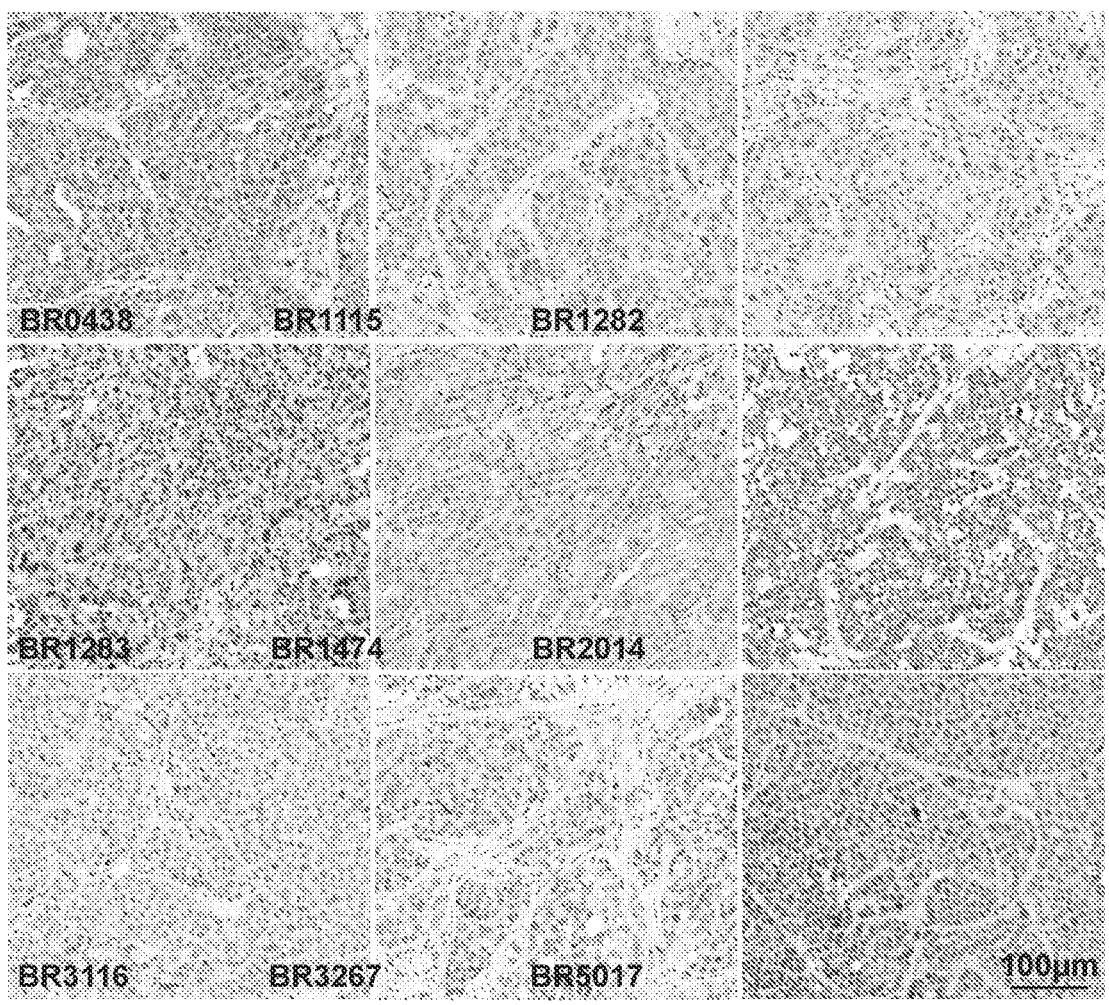
Figure 3E:
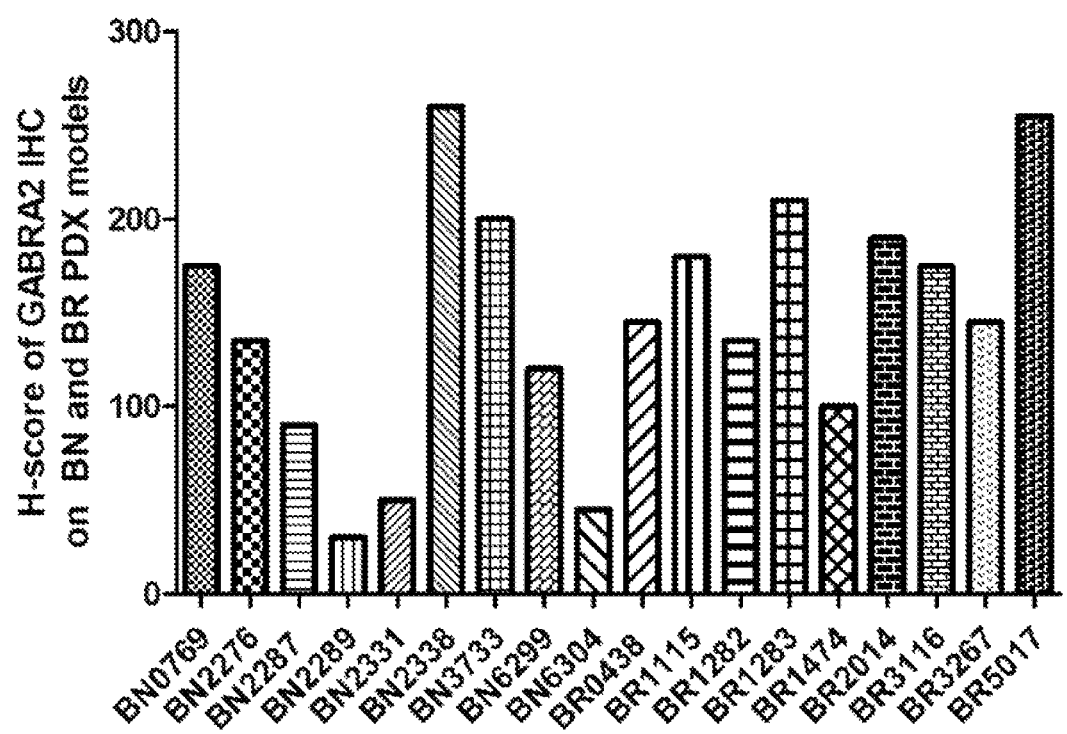

Sequential propagation of tumor derived xenografts (PDX) was used to identify novel CSC markers. To this end, GABRA2 mRNA expression levels were higher following sequential propagation of human MRT PDX compared to the primary tumor (FIG. 2A), indicating GABRA2 as a CSC biomarker. Further, GABRA2 mRNA expression levels were upregulated in a progressive manner through-out the serial propagation. Most importantly, GABRA2 was enriched in the ALDHIAI positive subpopulation of sequentially propagated (Xn9) MRT, which is representing an enriched population of CSCs (FIG. 2B).

Following, positive GABRA2 immunohistochemistry staining performed on 9 different brain cancer and 9 nine different breast cancer tissues validated expression of GABRA2 in cancerous tissues at the protein level (FIGS. 3A-E).

Example 2

Generation of an Anti-Human-GABRA2 Monoclonal Antibody

Figure 5A:
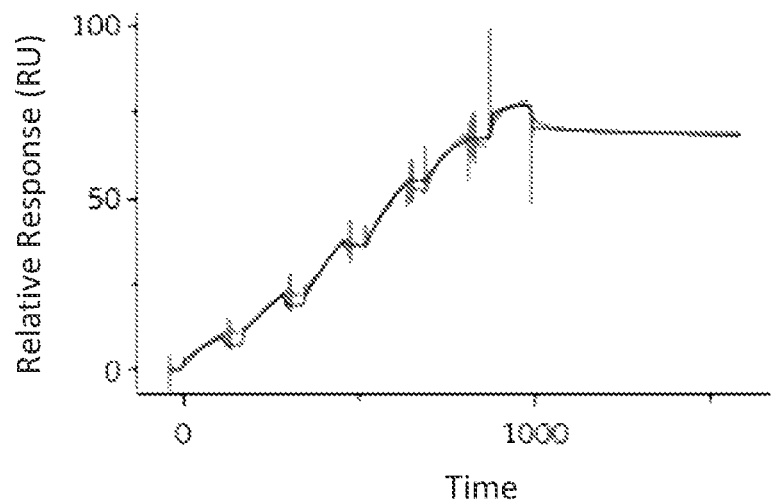
FIGS. 5A-B demonstrate affinity of antibody U6882DH130_13 to GABRA2, as determined by Biacore analysis.
Figure 5B:
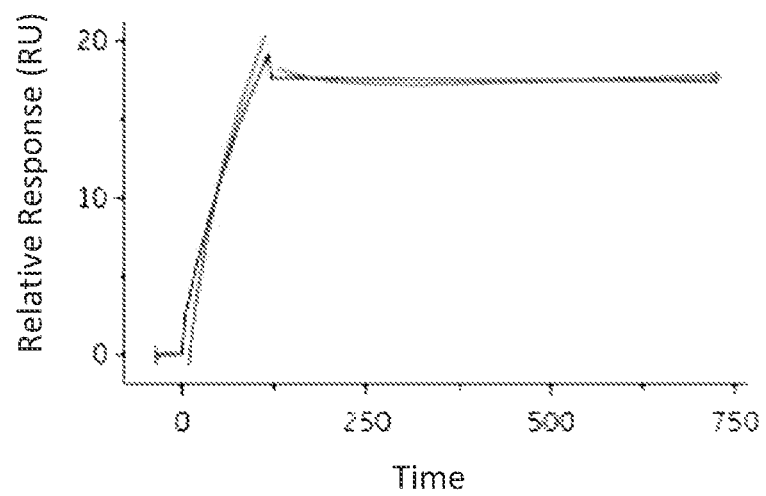

Several monoclonal hybridomas were generated against the human GABRA2 antigen (Table 1 hereinbelow). Following, purity, binding specificity and kinetics and the sequence of an anti-GABRA2 antibody, referred to herein as U6882DH130_13, purified from a hybridoma clone, referred to herein as 10C5B9, were determined. Western blot and indirect ELISA assay using plates coated with human GABRA2 (FIG. 4 and Table 2 hereinbelow) verified the antibody is pure and capable of binding GABRA2. Biacore analysis indicated that the affinity of the antibody to GABRA2 is $3.88 \times 10^{-10}$ (FIGS. 5A-B and Table 3 hereinbelow). The heavy chain nucleic acids and amino acids sequences are shown in FIG. 6 (SEQ ID NO: 1 and 6, respectively) and the light chain nucleic acids and amino acids sequences are shown in FIG. 7 (SEQ ID NO: 11 and 16, respectively). In addition, the antibody was stable at 2-8° C. for up to 1 month and at 20° C. for up to two years.

TABLE 1

Hybridomas generated against the human GABRA2 antigen

| Hybridoma Clone ID | Isotype |
|---|---|
| 9A11F7 | IgG2b, K |
| 9D4E12 | IgG2b, K |
| 9G8B11 | IgG2b, K |
| 10C5B9 | IgG2b, K |
| 10F1E11 | IgG2a, K |

TABLE 2

ELISA results of antibody U6882DH130_13 secreted by hybridoma 10C5B9

| | Concentration (ng/ml) | | | | | | |
|---|---|---|---|---|---|---|---|
| Dilution | 1,000.00 1:1,000 | 500.00 1:2,000 | 250.00 1:4,000 | 125.00 1:8,000 | 62.50 1:16,000 | 31.25 1:32,000 | 15.62 1:64,000 |
| Antibody from clone10C5B9 | 2.003 0.065 | 1.968 0.057 | 1.998 0.058 | 1.984 0.061 | 1.788 0.060 | 1.654 0.060 | 1.373 0.059 |

TABLE 2-continued

ELISA results of antibody U6882DH130_13 secreted by hybridoma 10C5B9

| | Concentration (ng/ml) | | | | | |
|---|---|---|---|---|---|---|
| Dilution | 7.81 1:128,000 | 3.90 1:256,000 | 1.95 1:512,000 | Blank Blank | / Titer | / Coating |
| Antibody from clone10C5B9 | 1.103 0.063 | 0.790 0.065 | 0.495 0.064 | 0.076 0.061 | 1:512,000 <1:1,000 | A B |

\* The titer is the highest dilution with signal/blank ≥2.1, the OD450 in black is the average of two technical replicates.
\* The starting concentration of 1 mg/ml and the corresponding dilution ration is calculated based on the actual concentration.

TABLE 3

Affinity measurement of GABRA2 to antibody U6882DH130_13.

| Analysis model | Ligand | Analyte | Chi$^2$ (RU$^2$) | ka (1/Ms) | kd (1/s) | KD (M) | Rmax (RU) |
|---|---|---|---|---|---|---|---|
| Single-cycle kinetics | U6882DH130_13 Antibody | gABRa2 | 1.98E+00 | 1.40E+05 | 5.42E−05 | 3.88E−10 | 70.5 |
| Single-dosekinetics | U6882DH130_13 Antibody | gABRa2 | 3.81E−01 | 6.28E+04 | 1.58E−05 | 2.51E−10 | 33.5 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

REFERENCES

Other References are Cited Throughout the Application

Ailles, L. E., and Weissman, I. L. (2007). Cancer stem cells in solid tumors. Current opinion in biotechnology 18, 460-466.
Anders, S., McCarthy, D. J., Chen, Y., Okoniewski, M., Smyth, G. K., Huber, W., and Robinson, M. D. (2013). Count-based differential expression analysis of RNA sequencing data using R and Bioconductor. Nature protocols 8, 1765-1786.
Ball, C. R., Oppel, F., Ehrenberg, K. R., Dubash, T. D., Dieter, S. M., Hoffmann, C. M., Abel, U., Herbst, F., Koch, M., Werner, J., et al. (2017). Succession of transiently active tumor-initiating cell clones in human pancreatic cancer xenografts. EMBO molecular medicine 9, 918-932.
Barker, H. E., Cox, T. R., and Erler, J. T. (2012). The rationale for targeting the LOX family in cancer. Nature reviews 12, 540-552.
Batle, E., and Clevers, H. (2017). Cancer stem cells revisited. Nature medicine 23, 1124-1134.
Bertucci, F., Bouvier-Labit, C., Finetti, P., Metellus, P., Adelaide, J., Mokhtari, K., Figarella-Branger, D., Decouvelaere, A. V., Miquel, C., Coindre, J. M., et al. (2013). Gene expression profiling of solitary fibrous tumors. PloS one 8, e64497.
Bondareva, A., Downey, C. M., Ayres, F., Liu, W., Boyd, S. K., Hallgrimsson, B., and Jirik, F. R. (2009). The lysyl oxidase inhibitor, beta-aminopropionitrile, diminishes the metastatic colonization potential of circulating breast cancer cells. PloS one 4, e5620.
Boufraqech, M., Zhang, L., Nilubol, N., Sadowski, S. M., Kotian, S., Quezado, M., and Kebebew, E. (2016). Lysyl Oxidase (LOX) Transcriptionally Regulates SNAI2 Expression and TIMP4 Secretion in Human Cancers. Clin Cancer Res 22, 4491-4504.
Cox, T. R., Rumney, R. M. H., Schoof, E. M., Perryman, L., Hoye, A. M., Agrawal, A., Bird, D., Latif, N. A., Forrest, H., Evans, H. R., et al. (2015). The hypoxic cancer secretome induces pre-metastatic bone lesions through lysyl oxidase. Nature 522, 106-110.
De Donato, M., Petrillo, M., Martinelli, E., Filippetti, F., Zannoni, G. F., Scambia, G., and Gallo, D. (2017). Uncovering the role of nuclear Lysyl oxidase (LOX) in advanced high grade serous ovarian cancer. Gynecologic oncology 146, 170-178.
Deisch, J., Raisanen, J., and Rakheja, D. (2011). Immunohistochemical expression of embryonic stem cell markers in malignant rhabdoid tumors. Pediatric and developmental pathology: the official journal of the Society for Pediatric Pathology and the Paediatric Pathology Society 14, 353-359.
Dekel, B., Metsuyanim, S., Schmidt-Ott, K. M., Fridman, E., Jacob-Hirsch, J., Simon, A., Pinthus, J., Mor, Y., Barasch, J., Amariglio, N., et al. (2006). Multiple imprinted and sternness genes provide a link between normal and tumor progenitor cells of the developing human kidney. Cancer research 66, 6040-6049.
Dekel, B., Zangi, L., Shezen, E., Reich-Zeliger, S., Eventov-Friedman, S., Katchman, H., Jacob-Hirsch, J., Amariglio, N., Rechavi, G., Margalit, R., et al. (2006b). Isolation and characterization of nontubular sea-1+lin– multipotent stem/progenitor cells from adult mouse kidney. J Am Soc Nephrol 17, 3300-3314.

Edwards, L., Gupta, R., and Filipp, F. V. (2016). Hypermutation of DPYD Deregulates Pyrimidine Metabolism and Promotes Malignant Progression. Molecular cancer research: MCR 14, 196-206.

Fouani, L., Menezes, S. V., Paulson, M., Richardson, D. R., and Kovacevic, Z. (2017). Metals and metastasis: Exploiting the role of metals in cancer metastasis to develop novel anti-metastatic agents. Pharmacological research 115, 275-287.

Garvin, A. J., Re, G. G., Tarnowski, B. I., Hazen-Martin, D. J., and Sens, D. A. (1993). The G401 cell line, utilized for studies of chromosomal changes in Wilms' tumor, is derived from a rhabdoid tumor of the kidney. The American journal of pathology 142, 375-380.

Ginestier, C., Hur, M. H., Charafe-Jauffret, E., Monville, F., Dutcher, J., Brown, M., Jacquemier, J., Viens, P., Kleer, C. G., Liu, S., et al. (2007). ALDH1 is a marker of normal and malignant human mammary stem cells and a predictor of poor clinical outcome. Cell stem cell 1, 555-567.

Hu, Y., and Smyth, G. K. (2009). ELDA: extreme limiting dilution analysis for comparing depleted and enriched populations in stem cell and other assays. Journal of immunological methods 347, 70-78.

Iturbide, A., Garcia de Herreros, A., and Peiro, S. (2015). A new role for LOX and LOXL2 proteins in transcription regulation. The FEBS journal 282, 1768-1773.

Kordes, U., Gesk, S., Fruhwald, M. C., Graf, N., Leuschner, I., Hasselblatt, M., Jeibmann, A., Oyen, F., Peters, O., Pietsch, T., et al. (2003). Clinical and molecular features in patients with atypical teratoid rhabdoid tumor or malignant rhabdoid tumor. Genes, chromosomes & cancer 49, 176-181.

Laidlaw, K. M., Berhan, S., Liu, S., Silvestri, G., Holyoake, T. L., Frank, D. A., Aggarwal, B., Bonner, M. Y., Perrotti, D., Jorgensen, H. G., et al. (2016). Cooperation of imipramine blue and tyrosine kinase blockade demonstrates activity against chronic myeloid leukemia. Oncotarget 7, 51651-51664.

Liu, N., Cox, T. R., Cui, W., Adell, G., Holmlund, B., Ping, J., Jarlsfelt, I., Erler, J. T., and Sun, X. F. (2017). Nuclear expression of lysyl oxidase enzyme is an independent prognostic factor in rectal cancer patients. Oncotarget 8, 60015-60024.

Martinez-Cruzado, L., Tornin, J., Santos, L., Rodriguez, A., Garcia-Castro, J., Moris, F., and Rodriguez, R. Aldh1 Expression and Activity Increase During Tumor Evolution in Sarcoma Cancer Stem Cell Populations. Scientific reports 6, 27878.

Mello, M. L., Alvarenga, E. M., Vidal Bde, C., and Di Donato, A. (2011). Chromatin supraorganization, mitotic abnormalities and proliferation in cells with increased or down-regulated lox expression: Indirect evidence of a LOX-histone H1 interaction in vivo. Micron 42, 8-16.

Mello, M. L., Contente, S., Vidal, B. C., Planding, W., and Schenck, U. (1995). Modulation of ras transformation affecting chromatin supraorganization as assessed by image analysis. Experimental cell research 220, 374-382.

Melstrom, L. G., Bentrem, D. J., Salabat, M. R., Kennedy, T. J., Ding, X. Z., Strouch, M., Rao, S. M., Witt, R. C., Ternent, C. A., Talamonti, M. S., et al. (2008). Overexpression of 5-lipoxygenase in colon polyps and cancer and the effect of 5-LOX inhibitors in vitro and in a murine model. Clin Cancer Res 14, 6525-6530.

Metsuyanim, S., Harari-Steinberg, O., Buzhor, E., Omer, D., Pode-Shakked, N., Ben-Hur, H., Halperin, R., Schneider, D., and Dekel, B. (2009). Expression of stem cell markers in the human fetal kidney. PloS one 4, e6709.

Millanes-Romero, A., Herranz, N., Perrera, V., Iturbide, A., Loubat-Casanovas, J., Gil, J., Jenuwein, T., Garcia de Herreros, A., and Peiro, S. (2013). Regulation of heterochromatin transcription by Snail1/LOXL2 during epithelial-to-mesenchymal transition. Molecular cell 52, 746-757.

Mizikova, I., Palumbo, F., Tabi, T., Herold, S., Vadasz, I., Mayer, K., Seeger, W., and Morty, R. E. (2017). Perturbations to lysyl oxidase expression broadly influence the transcriptome of lung fibroblasts. Physiological genomics 49, 416-429.

Moore, L. S. (2011). Quiescent, slow-cycling stem cell populations in cancer: a review of the evidence and discussion of significance. J Oncol. 10.

Olson, T. A., Bayar, E., Kosnik, E., Hamoudi, A. B., Klopfenstein, K. J., Pieters, R. S., and Ruymann, F. B. (1995). Successful treatment of disseminated central nervous system malignant rhabdoid tumor. Journal of pediatric hematology/oncology 17, 71-75.

Parham, D. M., Weeks, D. A., and Beckwith, J. B. (1994). The clinicopathologic spectrum of putative extrarenal rhabdoid tumors. An analysis of 42 cases studied with immunohistochemistry or electron microscopy. The American journal of surgical pathology 18, 1010-1029.

Petrillo, L. A., Wolf, D. M., Kapoun, A. M., Wang N. J., Barczak, A., Xiao, Y., Korkaya, H., Baehner, F., Lewicki, J., Wicha, M., et al. (2012). Xenografts faithfully recapitulate breast cancer-specific gene expression patterns of parent primary breast tumors. Breast cancer research and treatment 135, 913-922.

Pleniceanu, O., Shukrun, R., Omer, D., Vax, E., Kanter, I., Dziedzic, K., Pode-Shakked, N., Mark-Daniei, M., Pri-Chen, S., Gnatek, Y., et al. (2017). Peroxisome proliferator-activated receptor gamma (PPARgamma) is central to the initiation and propagation of human angiomyolipoma, suggesting its potential as a therapeutic target. EMBO molecular medicine 9, 1763.

Pode-Shakked, N., Gershon, R., Tam, G., Omer, D., Gnatek, Y., Kanter, I., Oriel, S., Katz, G., Harari-Steinberg, O., Kalisky, T., et al. (2017). Evidence of In Vitro Preservation of Human Nephrogenesis at the Single-Cell Level. Stem Cell Reports 9, 279-291.

Pode-Shakked, N., Metsuyanim, S., Rom-Gross, E., Mor, Y., Fridman, E., Goldstein, I., Amariglio, N., Rechavi, G., Keshet, G., and Dekel, B. (2009). Developmental tumourigenesis: NCAM as a putative marker for the malignant renal stem/progenitor cell population. Journal of cellular and molecular medicine 13, 1792-1808.

Pode-Shakked, N., Shukrun, R., Mark-Danieli, M., Tsvetkov, P., Bahar, S., Pri-Chen, S., Goldstein, R. S., Rom-Gross, E., Mor, Y., Fridman, E., et al. (2013). The isolation and characterization of renal cancer initiating cells from human Wilms' tumour xenografts unveils new therapeutic targets. EMBO molecular medicine 5, 18-37.

Shukrun, R., Pode-Shakked, N., Pleniceanu, O., Omer, D., Vax, E., Peer, E., Pri-Chen, S., Jacob, J., Hu, Q., Harari-Steinberg, O., et al. (2014). Wilms' tumor blastemal stem cells dedifferentiate to propagate the tumor bulk. Stem Cell Reports 3, 24-33.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Thomas, C., and Karnoub, A. E. (2013). Lysyl oxidase at the crossroads of mesenchymal stem cells and epithelial-mesenchymal transition. Oncotarget 4, 376-377.

Tomita, H., Tanaka, K., Tanaka, T., and Hara, A. Aldehyde dehydrogenase 1A1 in stem cells and cancer. Oncotarget 7, 11018-11032.

Versteege, I., Sevenet, N., Lange, J., Rousseau-Merck, M. F., Ambros, P., Handgretinger, R., Aurias, A., and Delattre, O. (1998). Truncating mutations of hSNF5/INI1 in aggressive paediatric cancer. Nature 394, 203-206.

Vitte, J., Gao, F., Coppola, G., Judkins, A. R., and Giovannini, M. (2017). Timing of Smarcb1 and Nf2 inactivation determines schwannoma versus rhabdoid tumor development. Nature communications 8, 300.

Wick, M. R., Ritter, J. H., and Dehner, L. P. (1995). Malignant rhabdoid tumors: a clinicopathologic review and conceptual discussion. Seminars in diagnostic pathology 12, 233-248.

What is claimed is:

1. An antibody comprising an antigen recognition domain which specifically binds GABRA2 and comprises complementarity determining regions (CDRs) as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of said antibody.

2. The antibody of claim 1 comprising a heterologous therapeutic moiety.

3. A method of treating neuroblastoma in a subject in need thereof, the method comprising administering to the subject an effective amount of an antibody comprising an antigen recognition domain which specifically binds GABRA2 and comprises complementarity determining regions (CDRs) as set forth in SEQ ID NOs: 18, 19 and 20 arranged in a sequential order from N to C on a light chain of the antibody and CDRs as set forth in SEQ ID NOs: 8, 9 and 10 arranged in a sequential order from N to C on a heavy chain of said antibody, thereby treating the neuroblastoma.

* * * * *

SEQUENCE LISTING

<160> NUMBER OF SEQ ID NOS: 22

<210> SEQ ID NO 1
<211> LENGTH: 408
<212> TYPE: DNA
<213> ORGANISM: Artificial sequence
<220> FEATURE:
<223> OTHER INFORMATION: heavy chain nucleic acid sequence with signal
      sequence

<400> SEQUENCE: 1
atgaaatgca gctgggttat cttcttcctg atggcagtgg ttacaggggt caattcagag      60
gttcagctgc agcagtctgg ggcagagctt gtgaagccag gggcctcagt caagttgtcc     120
tgcacagctt ctggcttcaa cattaaagac acctatatgt attgggtgaa gcagaggcct     180
gaacagggcc tggagtggat tggaaggatt gatcctgcga atggtaatac taaatatgac     240
ccgaagttcc agggcaaggc cactataaca gcagacacat cctccaacac agcctacctg     300
cagctcagca gcctgacatc tgaggacact gccgtctatt actgtgctag taattactac     360
gggtcctttg actactgggg ccaaggcacc actctcacag tctcctca                  408

<210> SEQ ID NO 2
<211> LENGTH: 351
<212> TYPE: DNA
<213> ORGANISM: Artificial sequence
<220> FEATURE:
<223> OTHER INFORMATION: heavy chain nucleic acid sequence

<400> SEQUENCE: 2
gaggttcagc tgcagcagtc tggggcagag cttgtgaagc caggggcctc agtcaagttg      60
tcctgcacag cttctggctt caacattaaa gacacctata tgtattgggt gaagcagagg     120
cctgaacagg gcctggagtg gattggaagg attgatcctg cgaatggtaa tactaaatat     180
gacccgaagt tccagggcaa ggccactata acagcagaca catcctccaa cacagcctac     240
ctgcagctca gcagcctgac atctgaggac actgccgtct attactgtgc tagtaattac     300
tacgggtcct ttgactactg gggccaaggc accactctca cagtctcctc a              351

<210> SEQ ID NO 3
<211> LENGTH: 15
<212> TYPE: DNA
<213> ORGANISM: Artificial sequence
<220> FEATURE:
<223> OTHER INFORMATION: Complementarity-determining region (CDR)
      sequence

<400> SEQUENCE: 3
gacacctata tgtat                                                       15

<210> SEQ ID NO 4
<211> LENGTH: 51

```
<212> TYPE: DNA
<213> ORGANISM: Artificial sequence
<220> FEATURE:
<223> OTHER INFORMATION: Complementarity-determining region (CDR)
      sequence

<400> SEQUENCE: 4
aggattgatc ctgcgaatgg taatactaaa tatgacccga agttccaggg c            51

<210> SEQ ID NO 5
<211> LENGTH: 24
<212> TYPE: DNA
<213> ORGANISM: Artificial sequence
<220> FEATURE:
<223> OTHER INFORMATION: Complementarity-determining region (CDR)
      sequence

<400> SEQUENCE: 5
aattactacg ggtcctttga ctac                                          24

<210> SEQ ID NO 6
<211> LENGTH: 136
<212> TYPE: PRT
<213> ORGANISM: Artificial sequence
<220> FEATURE:
<223> OTHER INFORMATION: heavy chain amino acid sequence with signal
      sequence

<400> SEQUENCE: 6

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Thr Tyr Met Tyr Trp Val Lys Gln Arg Pro Glu Gln Gly Leu
    50                  55                  60

Glu Trp Ile Gly Arg Ile Asp Pro Ala Asn Gly Asn Thr Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Ser Asn Tyr Tyr Gly Ser Phe Asp Tyr Trp Gly Gln
        115                 120                 125

Gly Thr Thr Leu Thr Val Ser Ser
    130                 135

<210> SEQ ID NO 7
<211> LENGTH: 117
<212> TYPE: PRT
<213> ORGANISM: Artificial sequence
<220> FEATURE:
<223> OTHER INFORMATION: heavy chain amino acid sequence

<400> SEQUENCE: 7

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Trp Ile
        35                  40                  45
```

```
Gly Arg Ile Asp Pro Ala Asn Gly Asn Thr Lys Tyr Asp Pro Lys Phe
        50                  55                  60

Gln Gly Lys Ala Thr Ile Thr Ala Asp Thr Ser Asn Thr Ala Tyr
 65                  70                  75                  80

Leu Gln Leu Ser Ser Leu Thr Ser Glu Asp Thr Ala Val Tyr Tyr Cys
                85                  90                  95

Ala Ser Asn Tyr Tyr Gly Ser Phe Asp Tyr Trp Gly Gln Gly Thr Thr
            100                 105                 110

Leu Thr Val Ser Ser
        115

<210> SEQ ID NO 8
<211> LENGTH: 5
<212> TYPE: PRT
<213> ORGANISM: Artificial sequence
<220> FEATURE:
<223> OTHER INFORMATION: Complementarity-determining region (CDR)
      sequence

<400> SEQUENCE: 8

Asp Thr Tyr Met Tyr
1               5

<210> SEQ ID NO 9
<211> LENGTH: 17
<212> TYPE: PRT
<213> ORGANISM: Artificial sequence
<220> FEATURE:
<223> OTHER INFORMATION: Complementarity-determining region (CDR)
      sequence

<400> SEQUENCE: 9

Arg Ile Asp Pro Ala Asn Gly Asn Thr Lys Tyr Asp Pro Lys Phe Gln
1               5                   10                  15

Gly

<210> SEQ ID NO 10
<211> LENGTH: 8
<212> TYPE: PRT
<213> ORGANISM: Artificial sequence
<220> FEATURE:
<223> OTHER INFORMATION: Complementarity-determining region (CDR)
      sequence

<400> SEQUENCE: 10

Asn Tyr Tyr Gly Ser Phe Asp Tyr
1               5

<210> SEQ ID NO 11
<211> LENGTH: 378
<212> TYPE: DNA
<213> ORGANISM: Artificial sequence
<220> FEATURE:
<223> OTHER INFORMATION: light chain nucleic acid sequence with signal
      sequence

<400> SEQUENCE: 11
atgtcctctg ctcagttcct tggtctcctg ttgctctgtt ttcaaggtac cagatgtgat      60
atccagatga cacagactac atcctccctg tctgcctctc tgggagacag agtcaccatc     120
agttgcaggg caagtcagga cattagcaat tatttaaact ggtatcagca gaaaccagat     180
ggaactgtta aactcctgat ctactacaca tcaagattac actcaggagt cccatcaagg     240
```

```
ttcagtggca gtgggtctgg aacagattat tctctcacca ttagcaacct ggagcaagaa    300
gatattgcca cttactttg ccaacagggt aatacgcttc ctccgacgtt cggtggaggc    360
accaagctgg aaatcaaa                                                  378
```

```
<210> SEQ ID NO 12
<211> LENGTH: 321
<212> TYPE: DNA
<213> ORGANISM: Artificial sequence
<220> FEATURE:
<223> OTHER INFORMATION: light chain nucleic acid sequence

<400> SEQUENCE: 12
```

```
gatatccaga tgacacagac tacatcctcc ctgtctgcct ctctgggaga cagagtcacc     60
atcagttgca gggcaagtca ggacattagc aattatttaa actggtatca gcagaaacca    120
gatggaactg ttaaactcct gatctactac acatcaagat tacactcagg agtcccatca    180
aggttcagtg gcagtgggtc tggaacagat tattctctca ccattagcaa cctggagcaa    240
gaagatattg ccacttactt tgccaacag ggtaatacgc ttcctccgac gttcggtgga    300
ggcaccaagc tggaaatcaa a                                              321
```

```
<210> SEQ ID NO 13
<211> LENGTH: 33
<212> TYPE: DNA
<213> ORGANISM: Artificial sequence
<220> FEATURE:
<223> OTHER INFORMATION: Complementarity-determining region (CDR)
      sequence

<400> SEQUENCE: 13
```

```
agggcaagtc aggacattag caattattta aac                                  33
```

```
<210> SEQ ID NO 14
<211> LENGTH: 21
<212> TYPE: DNA
<213> ORGANISM: Artificial sequence
<220> FEATURE:
<223> OTHER INFORMATION: Complementarity-determining region (CDR)
      sequence

<400> SEQUENCE: 14
```

```
tacacatcaa gattacactc a                                               21
```

```
<210> SEQ ID NO 15
<211> LENGTH: 27
<212> TYPE: DNA
<213> ORGANISM: Artificial sequence
<220> FEATURE:
<223> OTHER INFORMATION: Complementarity-determining region (CDR)
      sequence

<400> SEQUENCE: 15
```

```
caacagggta atacgcttcc tccgacg                                         27
```

```
<210> SEQ ID NO 16
<211> LENGTH: 126
<212> TYPE: PRT
<213> ORGANISM: Artificial sequence
<220> FEATURE:
<223> OTHER INFORMATION: light chain amino acid sequence with signal
      sequence
```

<400> SEQUENCE: 16

Met Ser Ser Ala Gln Phe Leu Gly Leu Leu Leu Cys Phe Gln Gly
1               5                   10                  15

Thr Arg Cys Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Asn Tyr Leu Asn Trp Tyr Gln Gln Lys Pro Asp Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Pro Thr Phe Gly Gly Gly Thr Lys Leu Glu Ile Lys
        115                 120                 125

<210> SEQ ID NO 17
<211> LENGTH: 107
<212> TYPE: PRT
<213> ORGANISM: Artificial sequence
<220> FEATURE:
<223> OTHER INFORMATION: light chain amino acid sequence

<400> SEQUENCE: 17

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 18
<211> LENGTH: 11
<212> TYPE: PRT
<213> ORGANISM: Artificial sequence
<220> FEATURE:
<223> OTHER INFORMATION: Complementarity-determining region (CDR) sequence

<400> SEQUENCE: 18

Arg Ala Ser Gln Asp Ile Ser Asn Tyr Leu Asn
1               5                   10

<210> SEQ ID NO 19
<211> LENGTH: 7
<212> TYPE: PRT
<213> ORGANISM: Artificial sequence
<220> FEATURE:

```
<223> OTHER INFORMATION: Complementarity-determining region (CDR)
      sequence

<400> SEQUENCE: 19

Tyr Thr Ser Arg Leu His Ser
1               5

<210> SEQ ID NO 20
<211> LENGTH: 9
<212> TYPE: PRT
<213> ORGANISM: Artificial sequence
<220> FEATURE:
<223> OTHER INFORMATION: Complementarity-determining region (CDR)
      sequence

<400> SEQUENCE: 20

Gln Gln Gly Asn Thr Leu Pro Pro Thr
1               5

<210> SEQ ID NO 21
<211> LENGTH: 223
<212> TYPE: PRT
<213> ORGANISM: Homo sapiens

<400> SEQUENCE: 21

Asn Ile Gln Glu Asp Glu Ala Lys Asn Asn Ile Thr Ile Phe Thr Arg
1               5                   10                  15

Ile Leu Asp Arg Leu Leu Asp Gly Tyr Asp Asn Arg Leu Arg Pro Gly
            20                  25                  30

Leu Gly Asp Ser Ile Thr Glu Val Phe Thr Asn Ile Tyr Val Thr Ser
        35                  40                  45

Phe Gly Pro Val Ser Asp Thr Asp Met Glu Tyr Thr Ile Asp Val Phe
    50                  55                  60

Phe Arg Gln Lys Trp Lys Asp Glu Arg Leu Lys Phe Lys Gly Pro Met
65                  70                  75                  80

Asn Ile Leu Arg Leu Asn Asn Leu Met Ala Ser Lys Ile Trp Thr Pro
                85                  90                  95

Asp Thr Phe Phe His Asn Gly Lys Lys Ser Val Ala His Asn Met Thr
            100                 105                 110

Met Pro Asn Lys Leu Leu Arg Ile Gln Asp Asp Gly Thr Leu Leu Tyr
        115                 120                 125

Thr Met Arg Leu Thr Val Gln Ala Glu Cys Pro Met His Leu Glu Asp
    130                 135                 140

Phe Pro Met Asp Ala His Ser Cys Pro Leu Lys Phe Gly Ser Tyr Ala
145                 150                 155                 160

Tyr Thr Thr Ser Glu Val Thr Tyr Ile Trp Thr Tyr Asn Ala Ser Asp
                165                 170                 175

Ser Val Gln Val Ala Pro Asp Gly Ser Arg Leu Asn Gln Tyr Asp Leu
            180                 185                 190

Leu Gly Gln Ser Ile Gly Lys Glu Thr Ile Lys Ser Ser Thr Gly Glu
        195                 200                 205

Tyr Thr Val Met Thr Ala His Phe His Leu Lys Arg Lys Ile Gly
    210                 215                 220

<210> SEQ ID NO 22
<211> LENGTH: 451
<212> TYPE: PRT
<213> ORGANISM: Homo sapiens
```

<400> SEQUENCE: 22

```
Met Lys Thr Lys Leu Asn Ile Tyr Asn Met Gln Phe Leu Leu Phe Val
1               5                   10                  15

Phe Leu Val Trp Asp Pro Ala Arg Leu Val Leu Ala Asn Ile Gln Glu
            20                  25                  30

Asp Glu Ala Lys Asn Asn Ile Thr Ile Phe Thr Arg Ile Leu Asp Arg
                35                  40                  45

Leu Leu Asp Gly Tyr Asp Asn Arg Leu Arg Pro Gly Leu Gly Asp Ser
        50                  55                  60

Ile Thr Glu Val Phe Thr Asn Ile Tyr Val Thr Ser Phe Gly Pro Val
65                  70                  75                  80

Ser Asp Thr Asp Met Glu Tyr Thr Ile Asp Val Phe Phe Arg Gln Lys
                85                  90                  95

Trp Lys Asp Glu Arg Leu Lys Phe Lys Gly Pro Met Asn Ile Leu Arg
            100                 105                 110

Leu Asn Asn Leu Met Ala Ser Lys Ile Trp Thr Pro Asp Thr Phe Phe
                115                 120                 125

His Asn Gly Lys Lys Ser Val Ala His Asn Met Thr Met Pro Asn Lys
        130                 135                 140

Leu Leu Arg Ile Gln Asp Asp Gly Thr Leu Leu Tyr Thr Met Arg Leu
145                 150                 155                 160

Thr Val Gln Ala Glu Cys Pro Met His Leu Glu Asp Phe Pro Met Asp
                165                 170                 175

Ala His Ser Cys Pro Leu Lys Phe Gly Ser Tyr Ala Tyr Thr Thr Ser
            180                 185                 190

Glu Val Thr Tyr Ile Trp Thr Tyr Asn Ala Ser Asp Ser Val Gln Val
                195                 200                 205

Ala Pro Asp Gly Ser Arg Leu Asn Gln Tyr Asp Leu Leu Gly Gln Ser
        210                 215                 220

Ile Gly Lys Glu Thr Ile Lys Ser Ser Thr Gly Glu Tyr Thr Val Met
225                 230                 235                 240

Thr Ala His Phe His Leu Lys Arg Lys Ile Gly Tyr Phe Val Ile Gln
                245                 250                 255

Thr Tyr Leu Pro Cys Ile Met Thr Val Ile Leu Ser Gln Val Ser Phe
            260                 265                 270

Trp Leu Asn Arg Glu Ser Val Pro Ala Arg Thr Val Phe Gly Val Thr
                275                 280                 285

Thr Val Leu Thr Met Thr Thr Leu Ser Ile Ser Ala Arg Asn Ser Leu
        290                 295                 300

Pro Lys Val Ala Tyr Ala Thr Ala Met Asp Trp Phe Ile Ala Val Cys
305                 310                 315                 320

Tyr Ala Phe Val Phe Ser Ala Leu Ile Glu Phe Ala Thr Val Asn Tyr
                325                 330                 335

Phe Thr Lys Arg Gly Trp Ala Trp Asp Gly Lys Ser Val Val Asn Asp
            340                 345                 350

Lys Lys Lys Glu Lys Ala Ser Val Met Ile Gln Asn Asn Ala Tyr Ala
        355                 360                 365

Val Ala Val Ala Asn Tyr Ala Pro Asn Leu Ser Lys Asp Pro Val Leu
370                 375                 380

Ser Thr Ile Ser Lys Ser Ala Thr Thr Pro Glu Pro Asn Lys Lys Pro
385                 390                 395                 400
```

-continued

```
Glu Asn Lys Pro Ala Glu Ala Lys Lys Thr Phe Asn Ser Val Ser Lys
            405                 410                 415

Ile Asp Arg Met Ser Arg Ile Val Phe Pro Val Leu Phe Gly Thr Phe
            420                 425                 430

Asn Leu Val Tyr Trp Ala Thr Tyr Leu Asn Arg Glu Pro Val Leu Gly
            435                 440                 445

Val Ser Pro
    450
```